United States Patent
Fletcher

(10) Patent No.: US 9,353,404 B2
(45) Date of Patent: May 31, 2016

(54) CAPTURE BASED NUCLEIC ACID DETECTION

(75) Inventor: Stephen John Fletcher, Toowong (AU)

(73) Assignee: Australian Centre for Plant Functional Genomics Pty Ltd, Urrbrae (AU)

( * ) Notice: Subject to any disclaimer, the term of this patent is extended or adjusted under 35 U.S.C. 154(b) by 376 days.

(21) Appl. No.: 13/823,730

(22) PCT Filed: Sep. 16, 2011

(86) PCT No.: PCT/AU2011/001184
§ 371 (c)(1),
(2), (4) Date: May 7, 2013

(87) PCT Pub. No.: WO2012/034177
PCT Pub. Date: Mar. 22, 2012

(65) Prior Publication Data
US 2013/0260377 A1    Oct. 3, 2013

(30) Foreign Application Priority Data
Sep. 16, 2010    (AU) .................. 2010904161

(51) Int. Cl.
*C12Q 1/68*    (2006.01)
*C07H 21/02*   (2006.01)
*C07H 21/04*   (2006.01)
*C07H 19/02*   (2006.01)

(52) U.S. Cl.
CPC ............. *C12Q 1/6813* (2013.01); *C07H 19/02* (2013.01); *C07H 21/04* (2013.01); *C12Q 1/682* (2013.01); *C12Q 1/6816* (2013.01); *C12Q 1/6837* (2013.01)

(58) Field of Classification Search
USPC ................. 435/6.1, 6.18; 536/23.1, 24.3, 24.5
See application file for complete search history.

(56) References Cited

U.S. PATENT DOCUMENTS

2006/0286583 A1*  12/2006  Luo et al. .................... 435/6

FOREIGN PATENT DOCUMENTS

WO    2008/122088 A1    10/2008
WO    2009/152566 A1    12/2009

OTHER PUBLICATIONS

International Search Report and Written Opinion received for PCT Patent Application No. PCT/AU2011/001184, mailed on Nov. 14, 2011, 7 pages.
International Preliminary Report on Patentability received for PCT Patent Application No. PCT/AU2011/001184, issued on Mar. 19, 2013, 6 pages.
Fletcher et al., "Toward Specific Detection of Dengue Virus Serotypes Using a Novel Modular Biosensor", Biosensors and Bioelectronics, vol. 26, Jul. 21, 2010, pp. 1696-1700.
Ikebukuro et al., "Novel Electrochemical Sensor System for Protein Using the Aptamers in Sandwich Manner", Biosensors and Bioelectronics, vol. 20, 2005, pp. 2168-2172.
Supplementary European Search Report prepared for European Application EP 11824356; Dec. 20, 2013; 3 pages.
Sun et al. "PCR-Free Quantification of Multiple Splice Variants in a Cancer Gene by Surface-Enhanced Raman Spectroscopy". J. Phys. Chem. B, Oct. 2009, 113: 14021-14025.
Zhang et al. "On-chip oligonucleotide ligation assay using one-dimensional microfluidic beads array for the detection of low-abundant DNA point mutations". Biosensors and Bioelectronics, Feb. 2008, 23: 945-951.
Zuo et al. "A novel sandwich assay with molecular beacon as report probe for nucleic acids detection on one-dimensional microfluidic beads array". Analytica Chimica Acta, Mar. 2007, 587: 9-13.

* cited by examiner

Primary Examiner — Robert T Crow
Assistant Examiner — Joseph G Dauner
(74) Attorney, Agent, or Firm — Morrison & Foerster LLP

(57) ABSTRACT

The present invention relates to methods and kits useful for the detection of a target nucleotide sequence in a sample. In general, the methods of the present invention are predicated on the target-mediated capture of a nuclease into a complex wherein the extent of complex formation, as measured by nuclease activity, is positively correlated with the presence of the target nucleic acid in the sample.

18 Claims, 18 Drawing Sheets

SEQUENCE LISTING

```
<160> NUMBER OF SEQ ID NOS: 98

<210> SEQ ID NO 1
<211> LENGTH: 35
<212> TYPE: DNA
<213> ORGANISM: Artificial Sequence
<220> FEATURE:
<223> OTHER INFORMATION: hygromycin resistance gene probe
<220> FEATURE:
<221> NAME/KEY: misc_feature
<222> LOCATION: (1)..(1)
<223> OTHER INFORMATION: dual biotin label

<400> SEQUENCE: 1
catcatcgaa attgccgtca accaagctct gatag                            35

<210> SEQ ID NO 2
<211> LENGTH: 21
<212> TYPE: DNA
<213> ORGANISM: Artificial Sequence
<220> FEATURE:
<223> OTHER INFORMATION: Hygromycin resistance gene probe helper 1

<400> SEQUENCE: 2
tggtcaagac caatgcggag c                                           21

<210> SEQ ID NO 3
<211> LENGTH: 22
```

```
<212> TYPE: DNA
<213> ORGANISM: Artificial Sequence
<220> FEATURE:
<223> OTHER INFORMATION: Hygromycin resistance gene probe helper 2

<400> SEQUENCE: 3
tcgcatcgac cctgcgccca ag                                              22

<210> SEQ ID NO 4
<211> LENGTH: 53
<212> TYPE: DNA
<213> ORGANISM: Artificial Sequence
<220> FEATURE:
<223> OTHER INFORMATION: Nuclease-capture aptamer Hyg_1

<400> SEQUENCE: 4
agtcgtggcg atcctgcaag ctccgtaccg aatcgaaaac gagttcaagg tac            53

<210> SEQ ID NO 5
<211> LENGTH: 47
<212> TYPE: DNA
<213> ORGANISM: Artificial Sequence
<220> FEATURE:
<223> OTHER INFORMATION: Nuclease-capture aptamer Hyg_2

<400> SEQUENCE: 5
atgcctccgc tcgaagtagt accgaatcga aaacgagttc aaggtac                   47

<210> SEQ ID NO 6
<211> LENGTH: 47
<212> TYPE: DNA
<213> ORGANISM: Artificial Sequence
<220> FEATURE:
<223> OTHER INFORMATION: Nuclease-capture aptamer Hyg_3

<400> SEQUENCE: 6
tcgtctggct aagatcggct accgaatcga aaacgagttc aaggtac                   47

<210> SEQ ID NO 7
<211> LENGTH: 24
<212> TYPE: DNA
<213> ORGANISM: Artificial Sequence
<220> FEATURE:
<223> OTHER INFORMATION: signaling molecule
<220> FEATURE:
<221> NAME/KEY: misc_feature
<222> LOCATION: (1)..(1)
<223> OTHER INFORMATION: fluorescein label
<220> FEATURE:
<221> NAME/KEY: misc_feature
<222> LOCATION: (24)..(24)
<223> OTHER INFORMATION: dabcyl label

<400> SEQUENCE: 7
gagaattcag ttttctgaat tctc                                            24

<210> SEQ ID NO 8
<211> LENGTH: 38
<212> TYPE: DNA
<213> ORGANISM: Artificial Sequence
<220> FEATURE:
<223> OTHER INFORMATION: 18S rRNA probe nucleotide sequence
<220> FEATURE:
<221> NAME/KEY: misc_feature
<222> LOCATION: (1)..(1)
<223> OTHER INFORMATION: 5' biotin-TEG label

<400> SEQUENCE: 8
```

```
tttctcaggc tccctctccg gaatcgaacc ctaattct                              38
```

<210> SEQ ID NO 9
<211> LENGTH: 20
<212> TYPE: DNA
<213> ORGANISM: Artificial Sequence
<220> FEATURE:
<223> OTHER INFORMATION: 18S rRNA assay helper 1 oligonucleotide

<400> SEQUENCE: 9

```
tcacccgtca ccaccatggt                                                 20
```

<210> SEQ ID NO 10
<211> LENGTH: 20
<212> TYPE: DNA
<213> ORGANISM: Artificial Sequence
<220> FEATURE:
<223> OTHER INFORMATION: 18S rRNA assay helper 2 oligonucleotide

<400> SEQUENCE: 10

```
ccttccttgg atgtggtagc                                                 20
```

<210> SEQ ID NO 11
<211> LENGTH: 20
<212> TYPE: DNA
<213> ORGANISM: Artificial Sequence
<220> FEATURE:
<223> OTHER INFORMATION: 18S rRNA assay helper 3 oligonucleotide

<400> SEQUENCE: 11

```
gagggccgtg cgatccgtcg                                                 20
```

<210> SEQ ID NO 12
<211> LENGTH: 20
<212> TYPE: DNA
<213> ORGANISM: Artificial Sequence
<220> FEATURE:
<223> OTHER INFORMATION: 18S rRNA assay helper 4 oligonucleotide

<400> SEQUENCE: 12

```
aatgcgcccc tcccggaagt                                                 20
```

<210> SEQ ID NO 13
<211> LENGTH: 20
<212> TYPE: DNA
<213> ORGANISM: Artificial Sequence
<220> FEATURE:
<223> OTHER INFORMATION: 18S rRNA assay helper 5 oligonucleotide

<400> SEQUENCE: 13

```
aatcatcgga tcagcgggcg                                                 20
```

<210> SEQ ID NO 14
<211> LENGTH: 50
<212> TYPE: DNA
<213> ORGANISM: Artificial Sequence
<220> FEATURE:
<223> OTHER INFORMATION: Nuclease-capture aptamer 18S_1

<400> SEQUENCE: 14

```
aatttgaatg atgcgtcgcc ggtaccgaat cgaaaacgag ttcaaggtac                50
```

<210> SEQ ID NO 15
<211> LENGTH: 48
<212> TYPE: DNA
<213> ORGANISM: Artificial Sequence

```
<220> FEATURE:
<223> OTHER INFORMATION: Nuclease-capture aptamer 18S_2

<400> SEQUENCE: 15
ccatcgaaag ttgatagggc taccgaatcg aaaacgagtt caaggtac          48

<210> SEQ ID NO 16
<211> LENGTH: 48
<212> TYPE: DNA
<213> ORGANISM: Artificial Sequence
<220> FEATURE:
<223> OTHER INFORMATION: Nuclease-capture aptamer 18S_3

<400> SEQUENCE: 16
ccgcgtcagc cttttatcta taccgaatcg aaaacgagtt caaggtac          48

<210> SEQ ID NO 17
<211> LENGTH: 45
<212> TYPE: DNA
<213> ORGANISM: Artificial Sequence
<220> FEATURE:
<223> OTHER INFORMATION: Green Fluorescent Protein probe
<220> FEATURE:
<221> NAME/KEY: misc_feature
<222> LOCATION: (1)..(1)
<223> OTHER INFORMATION: dual biotin label

<400> SEQUENCE: 17
gagagagaga ttcatgtggt cggggtagcg gctgaagcac tgcac             45

<210> SEQ ID NO 18
<211> LENGTH: 48
<212> TYPE: DNA
<213> ORGANISM: Artificial Sequence
<220> FEATURE:
<223> OTHER INFORMATION: Nuclease-capture aptamer GFP_1

<400> SEQUENCE: 18
cttgctcacc atggtattag taccgaatcg aaaacgagtt caaggtac          48

<210> SEQ ID NO 19
<211> LENGTH: 47
<212> TYPE: DNA
<213> ORGANISM: Artificial Sequence
<220> FEATURE:
<223> OTHER INFORMATION: Nuclease-capture aptamer GFP_2

<400> SEQUENCE: 19
acacgctgaa cttgtggcgt accgaatcga aaacgagttc aaggtac           47

<210> SEQ ID NO 20
<211> LENGTH: 48
<212> TYPE: DNA
<213> ORGANISM: Artificial Sequence
<220> FEATURE:
<223> OTHER INFORMATION: Nuclease-capture aptamer GFP_3

<400> SEQUENCE: 20
ccccttgttg aatacgcttg taccgaatcg aaaacgagtt caaggtac          48

<210> SEQ ID NO 21
<211> LENGTH: 50
<212> TYPE: DNA
<213> ORGANISM: Artificial Sequence
<220> FEATURE:
<223> OTHER INFORMATION: Nuclease-capture aptamer GFP_4
```

<400> SEQUENCE: 21
tagttgtact ccagcttgtg cctaccgaat cgaaaacgag ttcaaggtac                50

<210> SEQ ID NO 22
<211> LENGTH: 48
<212> TYPE: DNA
<213> ORGANISM: Artificial Sequence
<220> FEATURE:
<223> OTHER INFORMATION: Nuclease-capture aptamer GFP_5

<400> SEQUENCE: 22
ttgaagaaga tggtgcgctc taccgaatcg aaaacgagtt caaggtac                48

<210> SEQ ID NO 23
<211> LENGTH: 47
<212> TYPE: DNA
<213> ORGANISM: Artificial Sequence
<220> FEATURE:
<223> OTHER INFORMATION: Nuclease-capture aptamer GFP_6

<400> SEQUENCE: 23
agatcagatc ccatacaatt accgaatcga aaacgagttc aaggtac                47

<210> SEQ ID NO 24
<211> LENGTH: 48
<212> TYPE: DNA
<213> ORGANISM: Artificial Sequence
<220> FEATURE:
<223> OTHER INFORMATION: Nuclease-capture aptamer GFP_7

<400> SEQUENCE: 24
aactcacaac gtggcactgg taccgaatcg aaaacgagtt caaggtac                48

<210> SEQ ID NO 25
<211> LENGTH: 48
<212> TYPE: DNA
<213> ORGANISM: Artificial Sequence
<220> FEATURE:
<223> OTHER INFORMATION: Nuclease-capture aptamer GFP_8

<400> SEQUENCE: 25
gcaggtgtat cttatacacg taccgaatcg aaaacgagtt caaggtac                48

<210> SEQ ID NO 26
<211> LENGTH: 50
<212> TYPE: DNA
<213> ORGANISM: Artificial Sequence
<220> FEATURE:
<223> OTHER INFORMATION: Nuclease-capture aptamer GFP_9

<400> SEQUENCE: 26
gtaggtcagg gtggtcacga ggtaccgaat cgaaaacgag ttcaaggtac                50

<210> SEQ ID NO 27
<211> LENGTH: 48
<212> TYPE: DNA
<213> ORGANISM: Artificial Sequence
<220> FEATURE:
<223> OTHER INFORMATION: Nuclease-capture aptamer GFP_10

<400> SEQUENCE: 27
cggacttgaa gaagtcgtgc taccgaatcg aaaacgagtt caaggtac                48

<210> SEQ ID NO 28
<211> LENGTH: 48

```
<212> TYPE: DNA
<213> ORGANISM: Artificial Sequence
<220> FEATURE:
<223> OTHER INFORMATION: Nuclease-capture aptamer GFP_11

<400> SEQUENCE: 28
ggtaccttct gggcatcctt taccgaatcg aaaacgagtt caaggtac                    48

<210> SEQ ID NO 29
<211> LENGTH: 48
<212> TYPE: DNA
<213> ORGANISM: Artificial Sequence
<220> FEATURE:
<223> OTHER INFORMATION: Nuclease-capture aptamer GFP_12

<400> SEQUENCE: 29
ggatgttgcc gtcctccttg taccgaatcg aaaacgagtt caaggtac                    48

<210> SEQ ID NO 30
<211> LENGTH: 48
<212> TYPE: DNA
<213> ORGANISM: Artificial Sequence
<220> FEATURE:
<223> OTHER INFORMATION: Nuclease-capture aptamer GFP_13

<400> SEQUENCE: 30
atgatataga cgttgtggct taccgaatcg aaaacgagtt caaggtac                    48

<210> SEQ ID NO 31
<211> LENGTH: 48
<212> TYPE: DNA
<213> ORGANISM: Artificial Sequence
<220> FEATURE:
<223> OTHER INFORMATION: Nuclease-capture aptamer GFP_14

<400> SEQUENCE: 31
ggcacctgtc gccaggtggg taccgaatcg aaaacgagtt caaggtac                    48

<210> SEQ ID NO 32
<211> LENGTH: 48
<212> TYPE: DNA
<213> ORGANISM: Artificial Sequence
<220> FEATURE:
<223> OTHER INFORMATION: Nuclease-capture aptamer GFP_15

<400> SEQUENCE: 32
tcaagaagct tccagaggaa taccgaatcg aaaacgagtt caaggtac                    48

<210> SEQ ID NO 33
<211> LENGTH: 43
<212> TYPE: DNA
<213> ORGANISM: Artificial Sequence
<220> FEATURE:
<223> OTHER INFORMATION: Nuclease-capture aptamer GFP_16

<400> SEQUENCE: 33
ttgaagttca ccttgtaccg aatcgaaaac gagttcaagg tac                         43

<210> SEQ ID NO 34
<211> LENGTH: 43
<212> TYPE: DNA
<213> ORGANISM: Artificial Sequence
<220> FEATURE:
<223> OTHER INFORMATION: Nuclease-capture aptamer GFP_17

<400> SEQUENCE: 34
```
gtcctcgatg ttgtgtaccg aatcgaaaac gagttcaagg tac                43

<210> SEQ ID NO 35
<211> LENGTH: 44
<212> TYPE: DNA
<213> ORGANISM: Artificial Sequence
<220> FEATURE:
<223> OTHER INFORMATION: Nuclease-capture aptamer GFP_18

<400> SEQUENCE: 35
ttggggtctt tgctcatacc gaatcgaaaa cgagttcaag gtac               44

<210> SEQ ID NO 36
<211> LENGTH: 46
<212> TYPE: DNA
<213> ORGANISM: Artificial Sequence
<220> FEATURE:
<223> OTHER INFORMATION: Nuclease-capture aptamer GFP_19

<400> SEQUENCE: 36
gtccatgccg agagtgatta ccgaatcgaa aacgagttca aggtac             46

<210> SEQ ID NO 37
<211> LENGTH: 43
<212> TYPE: DNA
<213> ORGANISM: Artificial Sequence
<220> FEATURE:
<223> OTHER INFORMATION: Nuclease-capture aptamer GFP_20

<400> SEQUENCE: 37
gctttacttg tacagtaccg aatcgaaaac gagttcaagg tac                43

<210> SEQ ID NO 38
<211> LENGTH: 43
<212> TYPE: DNA
<213> ORGANISM: Artificial Sequence
<220> FEATURE:
<223> OTHER INFORMATION: Nuclease-capture aptamer GFP_21

<400> SEQUENCE: 38
tagatgcatg ctcgataccg aatcgaaaac gagttcaagg tac                43

<210> SEQ ID NO 39
<211> LENGTH: 43
<212> TYPE: DNA
<213> ORGANISM: Artificial Sequence
<220> FEATURE:
<223> OTHER INFORMATION: Nuclease-capture aptamer GFP_22

<400> SEQUENCE: 39
taggaatgct cgtcataccg aatcgaaaac gagttcaagg tac                43

<210> SEQ ID NO 40
<211> LENGTH: 43
<212> TYPE: DNA
<213> ORGANISM: Artificial Sequence
<220> FEATURE:
<223> OTHER INFORMATION: Nuclease-capture aptamer GFP_23

<400> SEQUENCE: 40
gctcgaggtt aacgataccg aatcgaaaac gagttcaagg tac                43

<210> SEQ ID NO 41
<211> LENGTH: 43
<212> TYPE: DNA
<213> ORGANISM: Artificial Sequence

```
<220> FEATURE:
<223> OTHER INFORMATION: Nuclease-capture aptamer GFP_24

<400> SEQUENCE: 41
tacctcagat cttcttaccg aatcgaaaac gagttcaagg tac                43

<210> SEQ ID NO 42
<211> LENGTH: 55
<212> TYPE: DNA
<213> ORGANISM: Artificial Sequence
<220> FEATURE:
<223> OTHER INFORMATION: Poly-A tail nuclease-capture aptamer GFP_25

<400> SEQUENCE: 42
tttttttttt tttttttttt tttttgtac cgaatcgaaa acgagttcaa ggtac     55

<210> SEQ ID NO 43
<211> LENGTH: 47
<212> TYPE: DNA
<213> ORGANISM: Artificial Sequence
<220> FEATURE:
<223> OTHER INFORMATION: Nuclease-capture aptamer Hyg_4

<400> SEQUENCE: 43
gtctgctgct ccatacaagt accgaatcga aacgagttc aaggtac             47

<210> SEQ ID NO 44
<211> LENGTH: 47
<212> TYPE: DNA
<213> ORGANISM: Artificial Sequence
<220> FEATURE:
<223> OTHER INFORMATION: Nuclease-capture aptamer Hyg_5

<400> SEQUENCE: 44
tgtccgtcag gacattgttt accgaatcga aacgagttc aaggtac             47

<210> SEQ ID NO 45
<211> LENGTH: 47
<212> TYPE: DNA
<213> ORGANISM: Artificial Sequence
<220> FEATURE:
<223> OTHER INFORMATION: Nuclease-capture aptamer Hyg_6

<400> SEQUENCE: 45
gcatcagctc atcgagagct accgaatcga aacgagttc aaggtac             47

<210> SEQ ID NO 46
<211> LENGTH: 46
<212> TYPE: DNA
<213> ORGANISM: Artificial Sequence
<220> FEATURE:
<223> OTHER INFORMATION: Nuclease-capture aptamer Hyg_7

<400> SEQUENCE: 46
ggtgtcgtcc atcacagtta ccgaatcgaa acgagttca aggtac              46

<210> SEQ ID NO 47
<211> LENGTH: 49
<212> TYPE: DNA
<213> ORGANISM: Artificial Sequence
<220> FEATURE:
<223> OTHER INFORMATION: Nuclease-capture aptamer Hyg_8

<400> SEQUENCE: 47
ggatcagcaa tcgcgcatat gtaccgaatc gaaaacgagt tcaaggtac          49
```

<210> SEQ ID NO 48
<211> LENGTH: 47
<212> TYPE: DNA
<213> ORGANISM: Artificial Sequence
<220> FEATURE:
<223> OTHER INFORMATION: Nuclease-capture aptamer Hyg_9

<400> SEQUENCE: 48
agcgatcgca tccatagcct accgaatcga aaacgagttc aaggtac        47

<210> SEQ ID NO 49
<211> LENGTH: 48
<212> TYPE: DNA
<213> ORGANISM: Artificial Sequence
<220> FEATURE:
<223> OTHER INFORMATION: Nuclease-capture aptamer Hyg_10

<400> SEQUENCE: 49
cagttcggtt tcaggcaggt taccgaatcg aaaacgagtt caaggtac       48

<210> SEQ ID NO 50
<211> LENGTH: 47
<212> TYPE: DNA
<213> ORGANISM: Artificial Sequence
<220> FEATURE:
<223> OTHER INFORMATION: Nuclease-capture aptamer Hyg_11

<400> SEQUENCE: 50
caacgtgaca ccctgtgcat accgaatcga aaacgagttc aaggtac        47

<210> SEQ ID NO 51
<211> LENGTH: 48
<212> TYPE: DNA
<213> ORGANISM: Artificial Sequence
<220> FEATURE:
<223> OTHER INFORMATION: Nuclease-capture aptamer Hyg_12

<400> SEQUENCE: 51
cgctaaactc cccaatgtca taccgaatcg aaaacgagtt caaggtac       48

<210> SEQ ID NO 52
<211> LENGTH: 43
<212> TYPE: DNA
<213> ORGANISM: Artificial Sequence
<220> FEATURE:
<223> OTHER INFORMATION: Nuclease-capture aptamer Hyg_13

<400> SEQUENCE: 52
acttccggaa tcgggtaccg aatcgaaaac gagttcaagg tac            43

<210> SEQ ID NO 53
<211> LENGTH: 45
<212> TYPE: DNA
<213> ORGANISM: Artificial Sequence
<220> FEATURE:
<223> OTHER INFORMATION: Nuclease-capture aptamer Hyg_14

<400> SEQUENCE: 53
gatgcaaagt gccgatatac cgaatcgaaa acgagttcaa ggtac          45

<210> SEQ ID NO 54
<211> LENGTH: 46
<212> TYPE: DNA
<213> ORGANISM: Artificial Sequence
<220> FEATURE:
<223> OTHER INFORMATION: Nuclease-capture aptamer Hyg_15

```
<400> SEQUENCE: 54
ataacgatct ttgtagaata ccgaatcgaa aacgagttca aggtac          46

<210> SEQ ID NO 55
<211> LENGTH: 45
<212> TYPE: DNA
<213> ORGANISM: Artificial Sequence
<220> FEATURE:
<223> OTHER INFORMATION: Nuclease-capture aptamer Hyg_16

<400> SEQUENCE: 55
atcggcgcag ctatttatac cgaatcgaaa acgagttcaa ggtac           45

<210> SEQ ID NO 56
<211> LENGTH: 45
<212> TYPE: DNA
<213> ORGANISM: Artificial Sequence
<220> FEATURE:
<223> OTHER INFORMATION: Nuclease-capture aptamer Hyg_17

<400> SEQUENCE: 56
caggacatat ccacgcctac cgaatcgaaa acgagttcaa ggtac           45

<210> SEQ ID NO 57
<211> LENGTH: 44
<212> TYPE: DNA
<213> ORGANISM: Artificial Sequence
<220> FEATURE:
<223> OTHER INFORMATION: Nuclease-capture aptamer Hyg_18

<400> SEQUENCE: 57
ctacatcgaa gctgaatacc gaatcgaaaa cgagttcaag gtac            44

<210> SEQ ID NO 58
<211> LENGTH: 46
<212> TYPE: DNA
<213> ORGANISM: Artificial Sequence
<220> FEATURE:
<223> OTHER INFORMATION: Nuclease-capture aptamer Hyg_19

<400> SEQUENCE: 58
acgagattct tcgccctcta ccgaatcgaa aacgagttca aggtac          46

<210> SEQ ID NO 59
<211> LENGTH: 45
<212> TYPE: DNA
<213> ORGANISM: Artificial Sequence
<220> FEATURE:
<223> OTHER INFORMATION: Nuclease-capture aptamer Hyg_20

<400> SEQUENCE: 59
gagctgcatc aggtcggtac cgaatcgaaa acgagttcaa ggtac           45

<210> SEQ ID NO 60
<211> LENGTH: 45
<212> TYPE: DNA
<213> ORGANISM: Artificial Sequence
<220> FEATURE:
<223> OTHER INFORMATION: Nuclease-capture aptamer Hyg_21

<400> SEQUENCE: 60
acttctcgac agacgtctac cgaatcgaaa acgagttcaa ggtac           45

<210> SEQ ID NO 61
```

```
<211> LENGTH: 43
<212> TYPE: DNA
<213> ORGANISM: Artificial Sequence
<220> FEATURE:
<223> OTHER INFORMATION: Nuclease-capture aptamer Hyg_22

<400> SEQUENCE: 61
gtgagttcag gcttttaccg aatcgaaaac gagttcaagg tac                43

<210> SEQ ID NO 62
<211> LENGTH: 45
<212> TYPE: DNA
<213> ORGANISM: Artificial Sequence
<220> FEATURE:
<223> OTHER INFORMATION: Nuclease-capture aptamer Hyg_23

<400> SEQUENCE: 62
acctcgtatt gggaatctac cgaatcgaaa acgagttcaa ggtac              45

<210> SEQ ID NO 63
<211> LENGTH: 46
<212> TYPE: DNA
<213> ORGANISM: Artificial Sequence
<220> FEATURE:
<223> OTHER INFORMATION: Nuclease-capture aptamer Hyg_24

<400> SEQUENCE: 63
gaacatcgcc tcgctccata ccgaatcgaa aacgagttca aggtac             46

<210> SEQ ID NO 64
<211> LENGTH: 45
<212> TYPE: DNA
<213> ORGANISM: Artificial Sequence
<220> FEATURE:
<223> OTHER INFORMATION: Nuclease-capture aptamer Hyg_25

<400> SEQUENCE: 64
ctccggatcg gacgattacc cgaatcgaaa acgagttcaa ggtac              45

<210> SEQ ID NO 65
<211> LENGTH: 47
<212> TYPE: DNA
<213> ORGANISM: Artificial Sequence
<220> FEATURE:
<223> OTHER INFORMATION: Nuclease-capture aptamer Hyg_26

<400> SEQUENCE: 65
tttgtgtacg cccgacagtt accgaatcga aaacgagttc aaggtac            47

<210> SEQ ID NO 66
<211> LENGTH: 45
<212> TYPE: DNA
<213> ORGANISM: Artificial Sequence
<220> FEATURE:
<223> OTHER INFORMATION: Nuclease-capture aptamer Hyg_27

<400> SEQUENCE: 66
cagacggccg cgcttcttac cgaatcgaaa acgagttcaa ggtac              45

<210> SEQ ID NO 67
<211> LENGTH: 46
<212> TYPE: DNA
<213> ORGANISM: Artificial Sequence
<220> FEATURE:
<223> OTHER INFORMATION: Nuclease-capture aptamer Hyg_28

<400> SEQUENCE: 67
```

```
acttctacac agccatcgta ccgaatcgaa aacgagttca aggtac          46
```

<210> SEQ ID NO 68
<211> LENGTH: 44
<212> TYPE: DNA
<213> ORGANISM: Artificial Sequence
<220> FEATURE:
<223> OTHER INFORMATION: Nuclease-capture aptamer Hyg_29

<400> SEQUENCE: 68

```
gtttccacta tcggcgtacc gaatcgaaaa cgagttcaag gtac             44
```

<210> SEQ ID NO 69
<211> LENGTH: 49
<212> TYPE: DNA
<213> ORGANISM: Artificial Sequence
<220> FEATURE:
<223> OTHER INFORMATION: Nuclease-capture aptamer Hyg_30

<400> SEQUENCE: 69

```
tggtcaagac caatgcggag ctaccgaatc gaaaacgagt tcaaggtac        49
```

<210> SEQ ID NO 70
<211> LENGTH: 50
<212> TYPE: DNA
<213> ORGANISM: Artificial Sequence
<220> FEATURE:
<223> OTHER INFORMATION: Nuclease-capture aptamer Hyg_31

<400> SEQUENCE: 70

```
tcgcatcgac cctgcgccca agtaccgaat cgaaaacgag ttcaaggtac       50
```

<210> SEQ ID NO 71
<211> LENGTH: 47
<212> TYPE: DNA
<213> ORGANISM: Artificial Sequence
<220> FEATURE:
<223> OTHER INFORMATION: Nuclease-capture aptamer Hyg_32

<400> SEQUENCE: 71

```
gtctgctgct ccatacaagt accgaatcga aaacgagttc aaggtac          47
```

<210> SEQ ID NO 72
<211> LENGTH: 46
<212> TYPE: DNA
<213> ORGANISM: Artificial Sequence
<220> FEATURE:
<223> OTHER INFORMATION: Nuclease-capture aptamer Hyg_33

<400> SEQUENCE: 72

```
atgaccgctg ttatgcggta ccgaatcgaa aacgagttca aggtac           46
```

<210> SEQ ID NO 73
<211> LENGTH: 45
<212> TYPE: DNA
<213> ORGANISM: Artificial Sequence
<220> FEATURE:
<223> OTHER INFORMATION: Nuclease-capture aptamer Hyg_34

<400> SEQUENCE: 73

```
gaaatccgcg tgcacgatac cgaatcgaaa acgagttcaa ggtac            45
```

<210> SEQ ID NO 74
<211> LENGTH: 48
<212> TYPE: DNA

```
<213> ORGANISM: Artificial Sequence
<220> FEATURE:
<223> OTHER INFORMATION: Nuclease-capture aptamer Hyg_35

<400> SEQUENCE: 74
ttcggggcag tcctcggccc taccgaatcg aaaacgagtt caaggtac           48

<210> SEQ ID NO 75
<211> LENGTH: 41
<212> TYPE: DNA
<213> ORGANISM: Artificial Sequence
<220> FEATURE:
<223> OTHER INFORMATION: Nuclease-capture aptamer Hyg_36

<400> SEQUENCE: 75
ccagtgatac ataccgaa tcgaaaacga gttcaaggta c                    41

<210> SEQ ID NO 76
<211> LENGTH: 48
<212> TYPE: DNA
<213> ORGANISM: Artificial Sequence
<220> FEATURE:
<223> OTHER INFORMATION: Nuclease-capture aptamer Hyg_37

<400> SEQUENCE: 76
gattccttgc ggtccgaatg taccgaatcg aaaacgagtt caaggtac           48

<210> SEQ ID NO 77
<211> LENGTH: 47
<212> TYPE: DNA
<213> ORGANISM: Artificial Sequence
<220> FEATURE:
<223> OTHER INFORMATION: Nuclease-capture aptamer Hyg_38

<400> SEQUENCE: 77
agcgatcgca tccatagcct accgaatcga aacgagttc aaggtac             47

<210> SEQ ID NO 78
<211> LENGTH: 48
<212> TYPE: DNA
<213> ORGANISM: Artificial Sequence
<220> FEATURE:
<223> OTHER INFORMATION: Nuclease-capture aptamer Hyg_39

<400> SEQUENCE: 78
gcgaccggtt gtagaacagc taccgaatcg aaaacgagtt caaggtac           48

<210> SEQ ID NO 79
<211> LENGTH: 55
<212> TYPE: DNA
<213> ORGANISM: Artificial Sequence
<220> FEATURE:
<223> OTHER INFORMATION: Poly-A tail nuclease-capture aptamer Hyg_40

<400> SEQUENCE: 79
tttttttttt tttttttttt tttttgtac cgaatcgaaa acgagttcaa ggtac    55

<210> SEQ ID NO 80
<211> LENGTH: 38
<212> TYPE: DNA
<213> ORGANISM: Artificial Sequence
<220> FEATURE:
<223> OTHER INFORMATION: Amine-tagged version of the 18S rRNA probe
<220> FEATURE:
<221> NAME/KEY: misc_feature
<222> LOCATION: (1)..(1)
<223> OTHER INFORMATION: Amine-12C tag
```

<400> SEQUENCE: 80
tttctcaggc tccctctccg gaatcgaacc ctaattct                                    38

<210> SEQ ID NO 81
<211> LENGTH: 67
<212> TYPE: DNA
<213> ORGANISM: Artificial Sequence
<220> FEATURE:
<223> OTHER INFORMATION: Hygromycin 18S rRNA linker 1

<400> SEQUENCE: 81
tttctcaggc tccctctccg gaatcgaacc ctaattcttg caagtcgtgg cgatcctgca           60
agctccg                                                                     67

<210> SEQ ID NO 82
<211> LENGTH: 54
<212> TYPE: DNA
<213> ORGANISM: Artificial Sequence
<220> FEATURE:
<223> OTHER INFORMATION: Hygromycin 18S rRNA linker 2

<400> SEQUENCE: 82
ctctccggaa tcgaacccta attcttgcaa gtcgtggcga tcctgcaagc tccg                 54

<210> SEQ ID NO 83
<211> LENGTH: 71
<212> TYPE: DNA
<213> ORGANISM: Artificial Sequence
<220> FEATURE:
<223> OTHER INFORMATION: Hygromycin 18S rRNA linker 3

<400> SEQUENCE: 83
tttctcaggc tccctctccg gaatcgaacc ctaattcttt catgttagtc gtggcgatcc           60
tgcaagctcc g                                                                71

<210> SEQ ID NO 84
<211> LENGTH: 72
<212> TYPE: DNA
<213> ORGANISM: Artificial Sequence
<220> FEATURE:
<223> OTHER INFORMATION: Hygromycin 18S rRNA linker 4

<400> SEQUENCE: 84
tttctcaggc tccctctccg gaatcgaacc ctaattctag tcggtgtcgt ccatcacagt           60
ttgccagtga ta                                                               72

<210> SEQ ID NO 85
<211> LENGTH: 72
<212> TYPE: DNA
<213> ORGANISM: Artificial Sequence
<220> FEATURE:
<223> OTHER INFORMATION: Hygromycin 18S rRNA linker 5

<400> SEQUENCE: 85
tttctcaggc tccctctccg gaatcgaacc ctaattcttt gaagcgatcg catccatagc           60
ctccgcgacc gg                                                               72

<210> SEQ ID NO 86
<211> LENGTH: 50
<212> TYPE: DNA
<213> ORGANISM: Artificial Sequence
<220> FEATURE:

```
<223> OTHER INFORMATION: Nuclease-capture aptamer 18S_4

<400> SEQUENCE: 86
aatttgaatg atgcgtcgcc ggtaccgaat cgaaaacgag ttcaaggtac                    50

<210> SEQ ID NO 87
<211> LENGTH: 48
<212> TYPE: DNA
<213> ORGANISM: Artificial Sequence
<220> FEATURE:
<223> OTHER INFORMATION: Nuclease-capture aptamer 18S_5

<400> SEQUENCE: 87
ccatcgaaag ttgatagggc taccgaatcg aaaacgagtt caaggtac                      48

<210> SEQ ID NO 88
<211> LENGTH: 48
<212> TYPE: DNA
<213> ORGANISM: Artificial Sequence
<220> FEATURE:
<223> OTHER INFORMATION: Nuclease-capture aptamer 18S_6

<400> SEQUENCE: 88
ccgcgtcagc cttttatcta taccgaatcg aaaacgagtt caaggtac                      48

<210> SEQ ID NO 89
<211> LENGTH: 52
<212> TYPE: DNA
<213> ORGANISM: Artificial Sequence
<220> FEATURE:
<223> OTHER INFORMATION: Nuclease-capture aptamer 18S_7

<400> SEQUENCE: 89
gatttaatga gccattcgca gttttaccga atcgaaaacg agttcaaggt ac                 52

<210> SEQ ID NO 90
<211> LENGTH: 47
<212> TYPE: DNA
<213> ORGANISM: Artificial Sequence
<220> FEATURE:
<223> OTHER INFORMATION: Nuclease-capture aptamer 18S_8

<400> SEQUENCE: 90
gttatttatt gtcactacct accgaatcga aaacgagttc aaggtac                       47

<210> SEQ ID NO 91
<211> LENGTH: 48
<212> TYPE: DNA
<213> ORGANISM: Artificial Sequence
<220> FEATURE:
<223> OTHER INFORMATION: Nuclease-capture aptamer 18S_9

<400> SEQUENCE: 91
gcaccagact tgccctccaa taccgaatcg aaaacgagtt caaggtac                      48

<210> SEQ ID NO 92
<211> LENGTH: 48
<212> TYPE: DNA
<213> ORGANISM: Artificial Sequence
<220> FEATURE:
<223> OTHER INFORMATION: Nuclease-capture aptamer 18S_10

<400> SEQUENCE: 92
tgcaacaact taaatatacg taccgaatcg aaaacgagtt caaggtac                      48
```

```
<210> SEQ ID NO 93
<211> LENGTH: 48
<212> TYPE: DNA
<213> ORGANISM: Artificial Sequence
<220> FEATURE:
<223> OTHER INFORMATION: Nuclease-capture aptamer 18S_11

<400> SEQUENCE: 93
gtgcctgccg tgaggcggac taccgaatcg aaaacgagtt caaggtac                    48

<210> SEQ ID NO 94
<211> LENGTH: 48
<212> TYPE: DNA
<213> ORGANISM: Artificial Sequence
<220> FEATURE:
<223> OTHER INFORMATION: Nuclease-capture aptamer 18S_12

<400> SEQUENCE: 94
cgatggcttg ctttgagcac taccgaatcg aaaacgagtt caaggtac                    48

<210> SEQ ID NO 95
<211> LENGTH: 48
<212> TYPE: DNA
<213> ORGANISM: Artificial Sequence
<220> FEATURE:
<223> OTHER INFORMATION: Nuclease-capture aptamer 18S_13

<400> SEQUENCE: 95
tcacccgtca ccaccatggt taccgaatcg aaaacgagtt caaggtac                    48

<210> SEQ ID NO 96
<211> LENGTH: 35
<212> TYPE: DNA
<213> ORGANISM: Artificial Sequence
<220> FEATURE:
<223> OTHER INFORMATION: 18S biotinylated capture probe
<220> FEATURE:
<221> NAME/KEY: misc_feature
<222> LOCATION: (35)..(35)
<223> OTHER INFORMATION: biotin-TEG tag

<400> SEQUENCE: 96
cgaaagttga tagggcagaa atttgaatga tgcgt                                  35

<210> SEQ ID NO 97
<211> LENGTH: 49
<212> TYPE: DNA
<213> ORGANISM: Artificial Sequence
<220> FEATURE:
<223> OTHER INFORMATION: 18S biotinylated capture aptamer
<220> FEATURE:
<221> NAME/KEY: misc_feature
<222> LOCATION: (1)..(1)
<223> OTHER INFORMATION: biotin tag

<400> SEQUENCE: 97
tctggaattt gaagccctgg gataccgaat cgaaaacgag ttcaaggta                   49

<210> SEQ ID NO 98
<211> LENGTH: 15
<212> TYPE: DNA
<213> ORGANISM: Artificial Sequence
<220> FEATURE:
<223> OTHER INFORMATION: EcoRI aptamer trigger

<400> SEQUENCE: 98
gttgaactcg tcttg                                                        15
```

US 9,353,404 B2

CAPTURE BASED NUCLEIC ACID DETECTION

CROSS REFERENCE TO RELATED APPLICATIONS

This is a U.S. National Phase patent application of international patent application PCT/AU2011/001184, filed on 16 Sep. 2011, which claims priority to Australian provisional patent application 2010904161 filed on 16 Sep. 2010, the content of which is herein incorporated by reference in their entirety.

SUBMISSION OF SEQUENCE LISTING ON ASCII TEXT FILE

The content of the following submission on ASCII text file is incorporated herein by reference in its entirety: a computer readable form (CRF) of the Sequence Listing (file name: 717232000100SubSeqList.txt, date recorded: Mar. 11, 2013, size: 21 KB).

FIELD OF THE INVENTION

The present invention relates to methods and kits useful for the detection of a target nucleotide sequence in a sample. In general, the methods of the present invention are predicated on the capture of a nuclease in order to generate a signal indicating the presence of a target nucleotide sequence in a sample.

BACKGROUND OF THE INVENTION

A range of molecular technologies for the detection of a target analyte in a sample have been developed. Such methods have application in, for example, public health, the detection of pathogens in food or water, epidemiological studies, genetically modified organism (GMO) detection, medicine, clinical diagnoses, disease susceptibility diagnoses, tissue typing, blood screening, forensic medicine, bioweapon detection, molecular toxicology, gene therapy, and DNA tagging, among many other applications.

Current methods for detecting an analyte such as a nucleic acid generally involve one, or a combination of, molecular techniques. These techniques generally fall into three groups loosely defined as sequence-specific detection, sequence-specific enrichment and signal amplification.

Most detection techniques gain their sequence specificity through base pairing of complementary probes or oligonucleotides to a sequence of interest within the target DNA sample.

The two most commonly used DNA detection methods, namely the polymerase chain reaction (PCR) and Southern blotting, differ in how they proceed from this point. The PCR method enriches a target DNA through a series of amplification cycles and signal detection can be, for example, through the use of stains, fluorescence or radiolabeling.

Southern blotting involves no DNA enrichment step, but uses high-energy $^{32}P$ for signal amplification. These extensively used techniques, although highly developed, still retain significant drawbacks. For PCR, the equipment required is expensive, the process is time-consuming and the degree of expertise required is high. Southern blotting often uses hazardous radioactive labeling, takes up to a week to complete, and requires large amounts of substrate DNA.

Reverse transcription polymerase chain reaction (RT-PCR) is a laboratory technique commonly used in molecular biology, which enables for the analysis of genes expressed from template DNA in cells. In RT-PCR, an RNA strand is first reverse transcribed into its DNA complement (complementary DNA, or cDNA) using the enzyme reverse transcriptase, and the resulting cDNA is amplified using conventional or real-time PCR. This approach is widely used to detect the expression of a gene or gene(s) in a given sample, and replaces the traditional Northern Blotting method. As described above, the laboratory equipment and reagents required for RT-PCR is expensive, the process is time-consuming and require a high degree of scientific training.

In light of the above, further methods for detecting analytes such as nucleic acids which are target-specific and sensitive would be desirable.

Reference to any prior art in this specification is not, and should not be taken as, an acknowledgment or any form of suggestion that this prior art forms part of the common general knowledge in any country.

SUMMARY OF THE INVENTION

The present invention is predicated on the development of a method for the capture of a nuclease in order to generate a signal indicating the presence of a target nucleotide sequence in a sample.

Accordingly, in a first aspect the present invention provides a method for detecting a target nucleic acid in a sample, the method comprising forming a reaction mix comprising:
  the sample;
  a nuclease;
  a solid substrate;
  a probe nucleic acid which is hybridisable under the conditions of the method to a first portion of the target nucleic acid, wherein the probe nucleic acid is immobilisable on the solid substrate; and
  a capture structure comprising a capture portion which is able to capture the nuclease and a targeting portion comprising a nucleotide sequence which is hybridisable under the conditions of the method to a second portion of the target nucleic acid;
  wherein the presence of the target nucleic acid in the sample allows the formation of a complex on the solid substrate wherein the complex comprises the probe nucleic acid, the target nucleic acid, the capture structure and a captured nuclease; and
  determining the extent of complex formation, wherein the extent of complex formation is positively correlated with the presence of the target nucleic acid in the sample.

In one embodiment, the target nucleic acid comprises DNA or RNA. When the target nucleic acid is RNA, the RNA may comprise rRNA or mRNA.

In some embodiments, the target nucleic acid is in a single-stranded state when contacted with the probe nucleic acid and the capture structure.

In some embodiments, the nuclease is a restriction endonuclease. In some embodiments, the nuclease is EcoRI.

In some embodiments, the capture portion of the capture structure comprises an aptamer.

In some embodiments, the method of the first aspect of the invention further comprises the addition of one or more helper oligonucleotides which bind to the target nucleic acid at a site adjacent to the binding site of the probe nucleic acid and/or a capture structure. In one embodiment, the binding site of the helper oligonucleotide on the target nucleic acid is separated from the binding site of the probe nucleic acid and/or a capture structure by a distance of three nucleotide residues.

In some embodiments, determining the extent of complex formation comprises measuring a residual nuclease activity in the reaction mix, wherein the extent of the residual nuclease activity is negatively correlated with the extent of complex formation.

Alternatively, in some embodiments, determining the extent of complex formation comprises measuring a nuclease activity associated with the complex, wherein the extent of nuclease activity associated with the complex is positively correlated with the extent of complex formation. In one embodiment, the method further comprises displacement of the nuclease from the complex and measurement of the displaced nuclease activity.

In some embodiments, a nuclease activity is determined by the rate or extent of cleavage of a reporter nucleotide sequence.

In some embodiments, the complex comprises a plurality of capture portions.

In some embodiments, multiple capture structures can bind to the target nucleic acid. In one embodiment, the multiple capture structures can bind to the target nucleic acid at multiple positions on the target nucleic acid.

In some embodiments, the capture structure further comprises a scaffold to which a plurality of capture portions can bind. In one embodiment, the scaffold comprises a nucleic acid. Alternatively, in one embodiment, the scaffold comprises a solid substrate.

In a second aspect the present invention provides a kit for performing the method of the first aspect of the invention, the kit comprising:
 a nuclease;
 a solid substrate;
 a probe nucleic acid which is hybridisable to a first portion of a target nucleic acid, wherein the probe nucleic acid is immobilisable on the solid substrate; and
 a capture structure comprising a capture portion which is able to capture the nuclease and a targeting portion comprising a nucleotide sequence which is hybridisable to a second portion of a target nucleic acid.

Increasing quantities of the target nucleic acid result in the capture and removal of more EcoRI molecules from the reaction solution and thus a reduction in total EcoRI activity, which is indicated by a reduced rate of digestion of signaling molecules.

Figure 11:
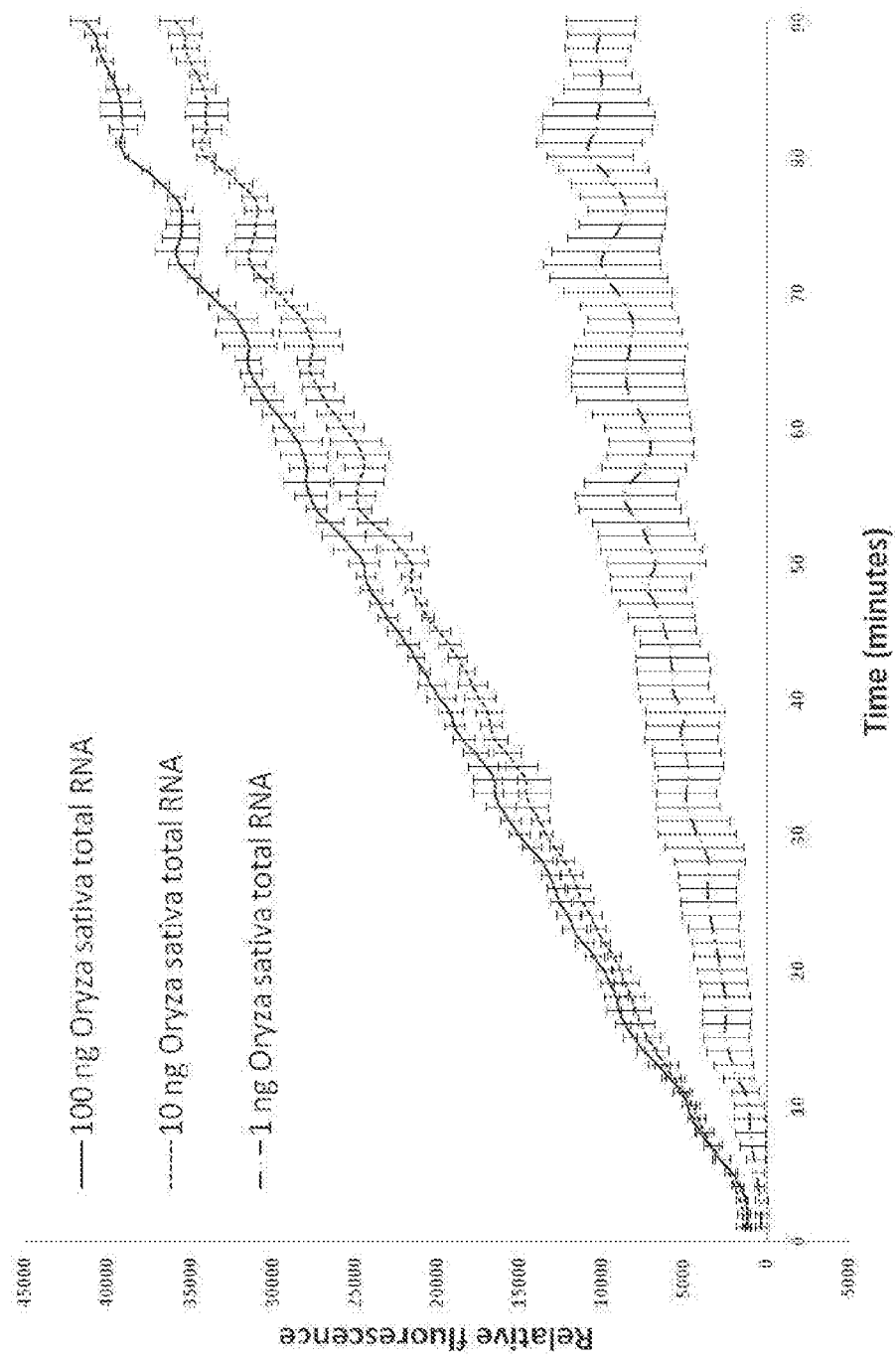

FIG. 11 demonstrates the semi-quantitative detection of 18S rRNA by an increased rate of relative signal generation as the amount of total RNA analysed increases. The error bars at each acquiring time point represent ±1 RSD (relative standard deviation).

Figure 12:
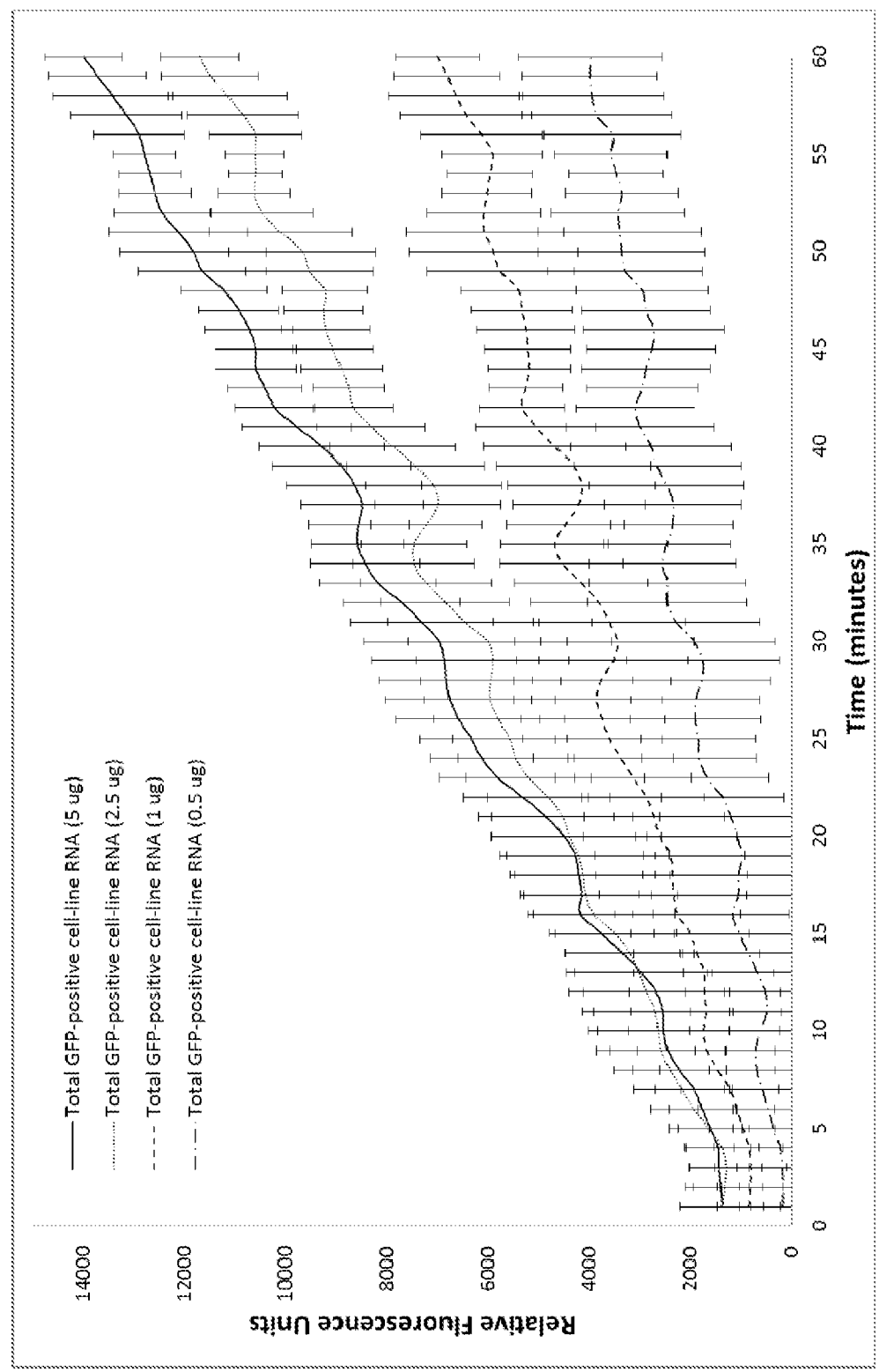

FIG. 12 shows a graph demonstrating the ability of the capture method to detect Green Fluorescent Protein (GFP) mRNA in a total RNA sample extracted from a GFP-positive human cell line. The graph shows an increase in relative fluorescence over time and indicates the presence of GFP mRNA in each total RNA treatment. Relative fluorescence was calculated by subtracting the average of each total RNA treatment fluorescence reading from the average of the water control readings at each acquiring time point. The error bars at each acquiring time point represent ±1 RSD (relative standard deviation).

Figure 13:
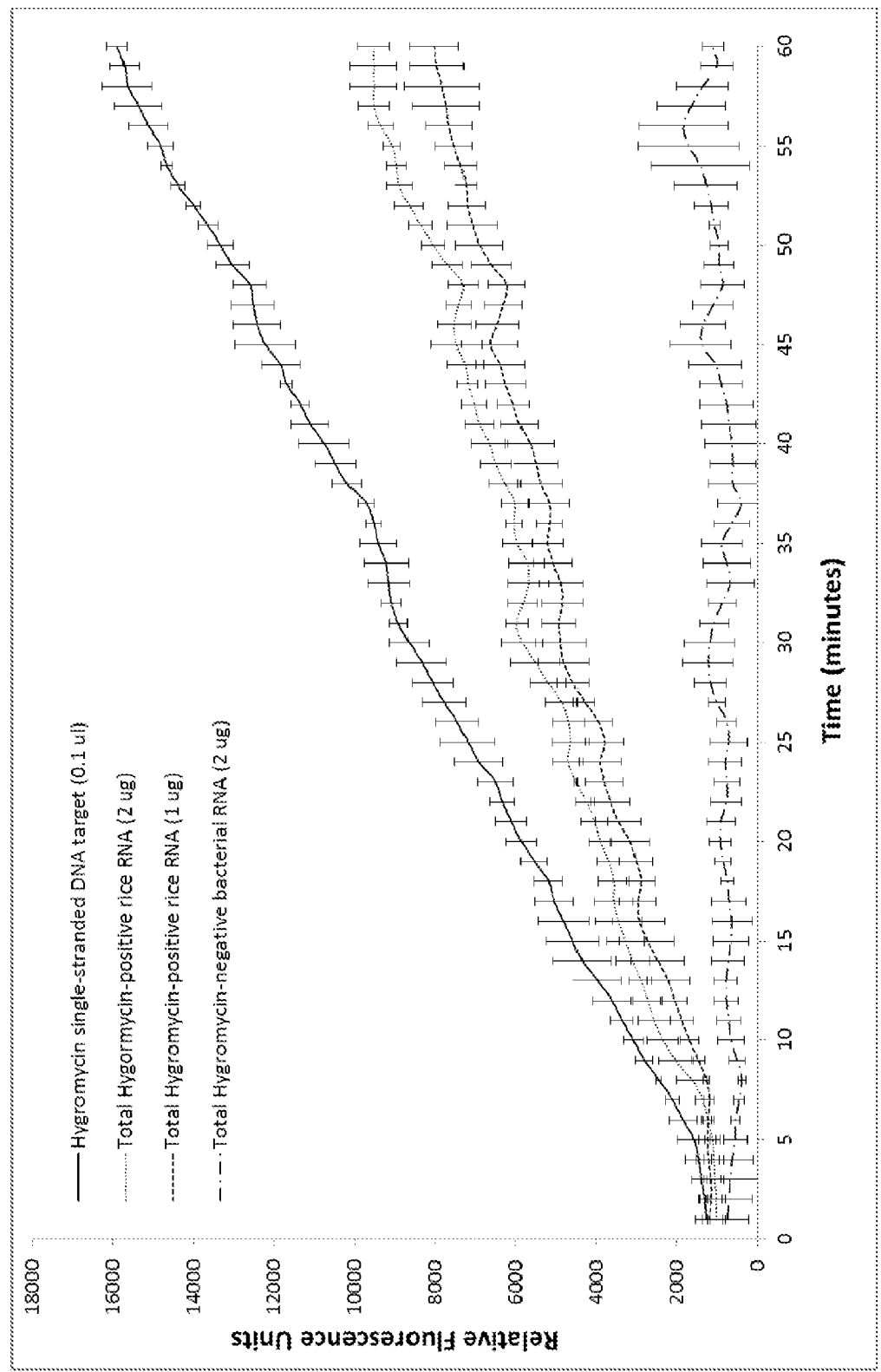

FIG. 13 shows a graph demonstrating the ability of the capture method to detect hygromycin mRNA in total RNA extracted from a rice leaf tissue. The graph shows an increase in relative fluorescence over time and indicates the presence of hygromycin mRNA in each total RNA treatment (except the total RNA control sample). Relative fluorescence was calculated by subtracting the average of each total RNA treatment fluorescence reading from the average of the water control readings at each acquiring time point. The error bars at each acquiring time point represent ±1 RSD (relative standard deviation).

Figure 14:
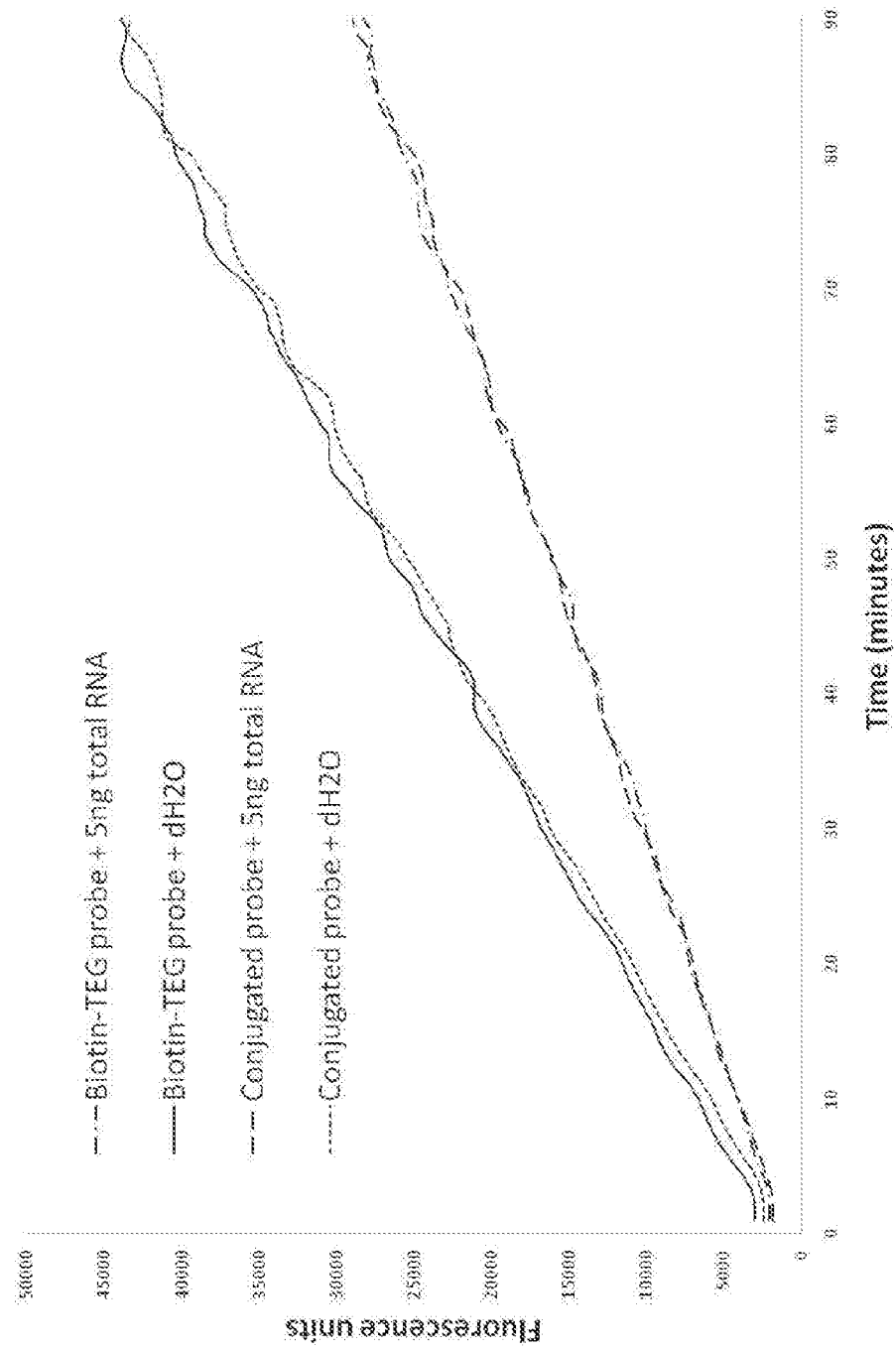

FIG. 14 shows that the signals generated for the total RNA and water treatments were not adversely impacted by the use of probes conjugated to a bead. The smooth lines represent the average of the fluorescence readings of two replicates at each acquiring time point. 5 ng of total RNA was chosen to ensure 18S rRNA detection was within its dynamic range for accurate comparison of the conjugated vs. biotin-TEG probe.

Figure 15:
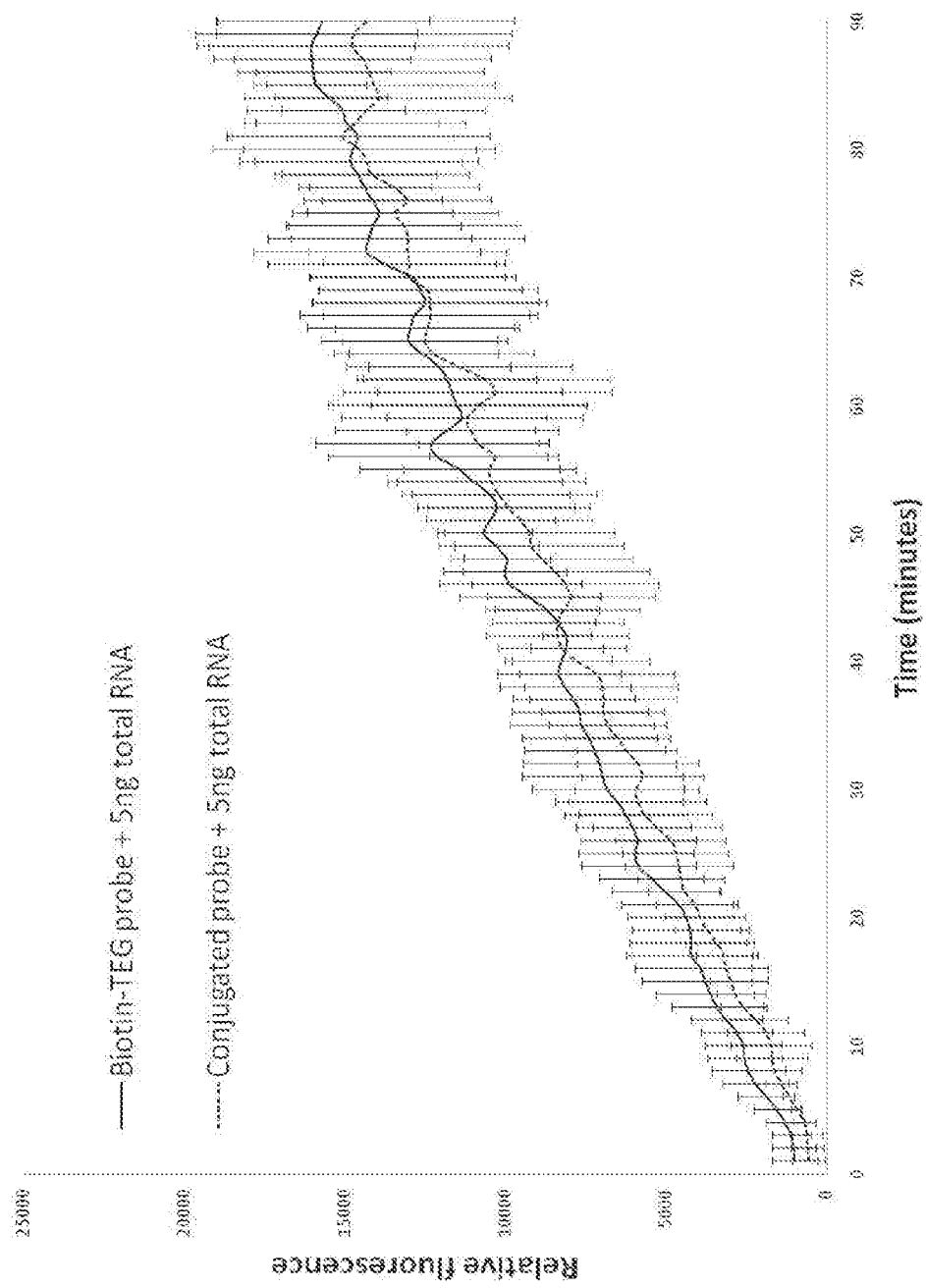

FIG. 15 shows the relative signals produced in assays using the probe-conjugated beads vs. the biotin-labeled probe/streptavidin-coated beads are not significantly different. The error bars at each acquiring time point represent ±1 RSD (relative standard deviation).

Figure 16:
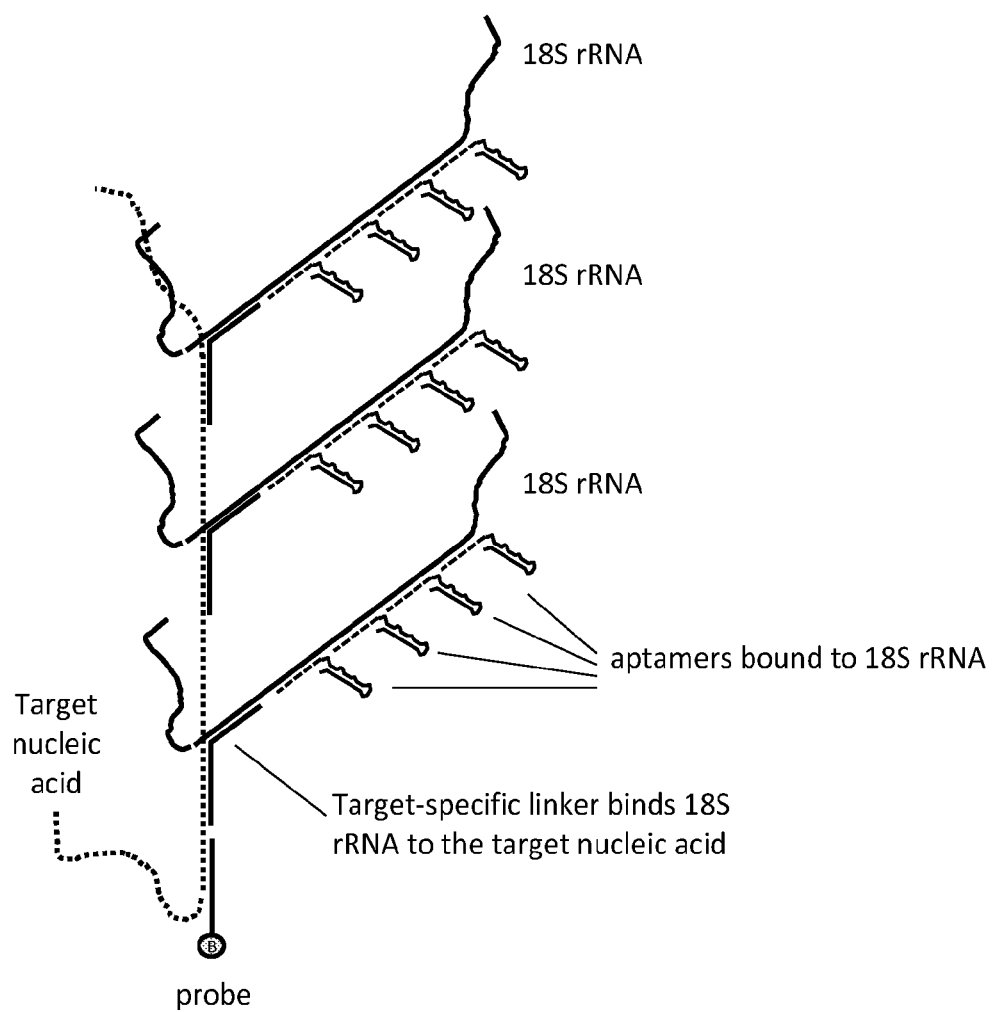

FIG. 16 illustrates an embodiment of the present invention for capturing multiple nuclease molecules for each target nucleic acid. In this instance, the presence of the target nucleic acid allows for the co-purification of one or more 18S rRNA molecules with multiple hybridised nuclease-capture aptamers. In this example, the 18S rRNA generally serves the function of a scaffold to which multiple capture agents may bind.

Figure 17:
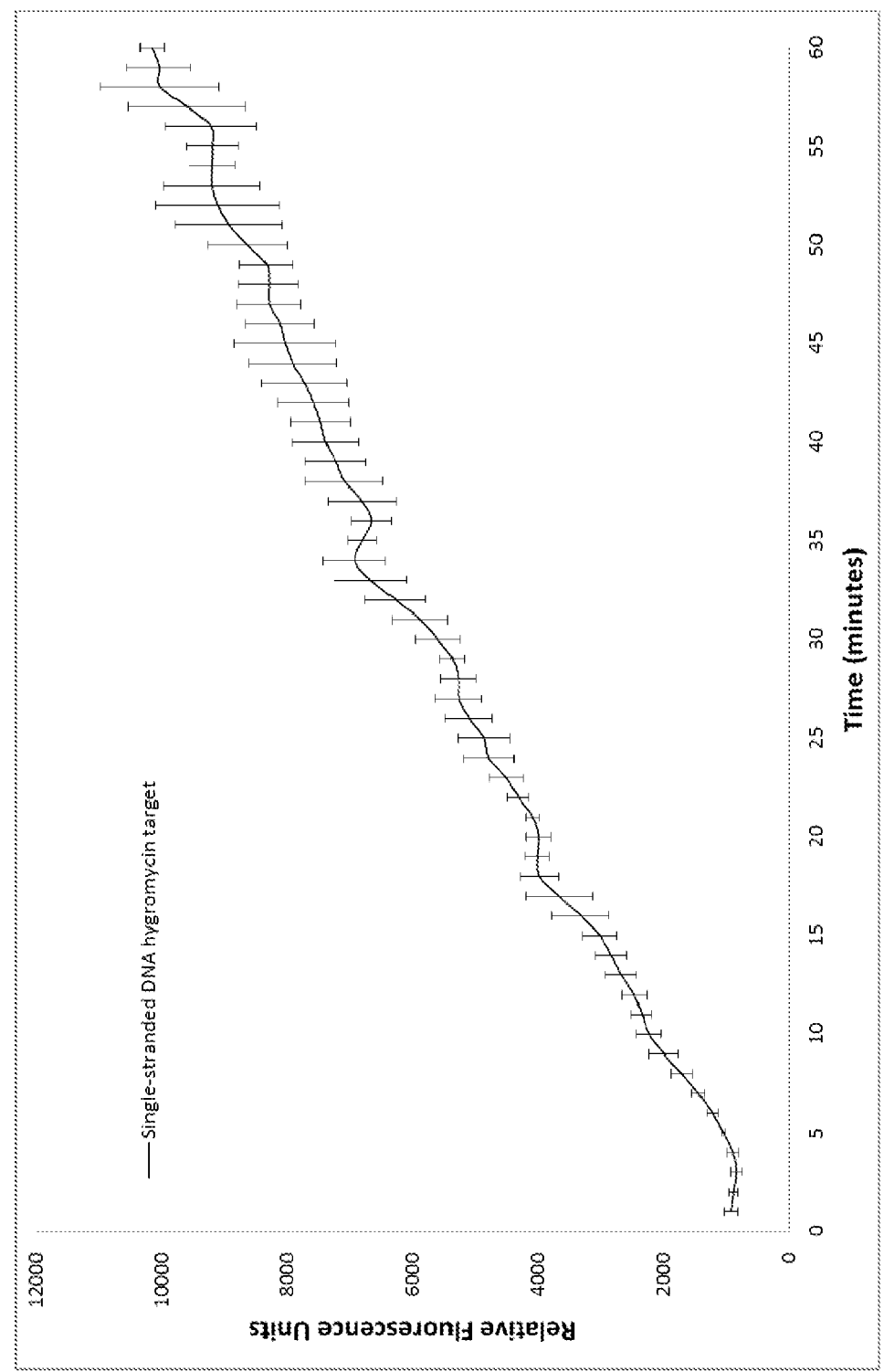

FIG. 17 shows a graph demonstrating the ability of the oligonucleotide scaffold approach to detect hygromycin single-stranded (ss) DNA. The graph shows an increase in relative fluorescence over time and indicates the detection of hygromycin ssDNA. Relative fluorescence was calculated by subtracting the average of the treatment fluorescence readings from the average of the water control readings at each acquiring time point. The error bars at each acquiring time point represent ±1 RSD (relative standard deviation).

Figure 18:
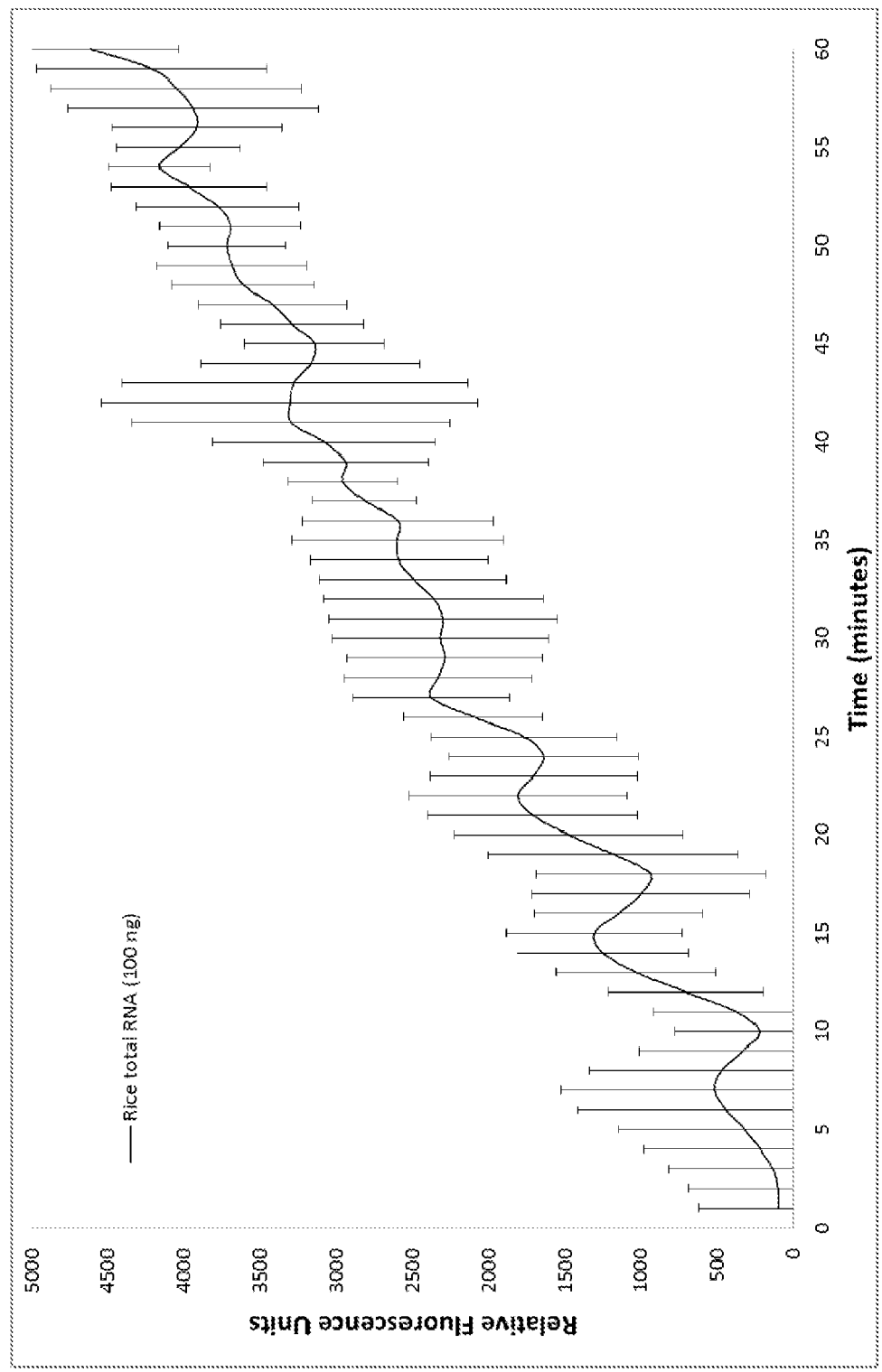

FIG. 18 shows a graph demonstrating the ability of the Nano-sphere scaffold approach to detect the presence of 18S rRNA in total RNA isolated from rice leaf tissue. Relative fluorescence was calculated by subtracting the average of the treatment fluorescence readings from the average of the bacterial total RNA negative control readings at each acquiring time point. The error bars at each acquiring time point represent ±1 RSD (relative standard deviation).

DESCRIPTION OF THE INVENTION

Nucleotide and amino acid sequences are referred to herein by a sequence identifier number (SEQ ID NO:). The SEQ ID NOs: correspond numerically to the sequence identifiers in the sequence listing, e.g. <400> 1 (SEQ ID NO:1), <400> 2 (SEQ ID NO: 2), etc. A summary of the sequence identifiers is provided in Table 1.

TABLE 1

Summary of Sequence Identifiers

| Sequence Identifier | Sequence |
|---|---|
| SEQ ID NO: 1 | Hygromycin resistance gene probe nucleotide sequence |
| SEQ ID NO: 2 | Hygromycin resistance gene probe helper 1 nucleotide sequence |
| SEQ ID NO: 3 | Hygromycin resistance gene probe helper 2 nucleotide sequence |
| SEQ ID NO: 4 | Nuclease-capture aptamer Hyg_1 nucleotide sequence |
| SEQ ID NO: 5 | Nuclease-capture aptamer Hyg_2 nucleotide sequence |
| SEQ ID NO: 6 | Nuclease-capture aptamer Hyg_3 nucleotide sequence |
| SEQ ID NO: 7 | Signaling molecule nucleotide sequence |
| SEQ ID NO: 8 | 18S rRNA probe nucleotide sequence |
| SEQ ID NO: 9 | 18S rRNA assay helper 1 nucleotide sequence |
| SEQ ID NO: 10 | 18S rRNA assay helper 2 nucleotide sequence |
| SEQ ID NO: 11 | 18S rRNA assay helper 3 nucleotide sequence |
| SEQ ID NO: 12 | 18S rRNA assay helper 4 nucleotide sequence |
| SEQ ID NO: 13 | 18S rRNA assay helper 5 nucleotide sequence |
| SEQ ID NO: 14 | Nuclease-capture aptamer 18S_1 nucleotide sequence |
| SEQ ID NO: 15 | Nuclease-capture aptamer 18S_2 nucleotide sequence |
| SEQ ID NO: 16 | Nuclease-capture aptamer 18S_3 nucleotide sequence |
| SEQ ID NO: 17 | GFP dual biotinylated probe nucleotide sequence |
| SEQ ID NO: 18 | Nuclease-capture aptamer GFP_1 nucleotide sequence |
| SEQ ID NO: 19 | Nuclease-capture aptamer GFP_2 nucleotide sequence |
| SEQ ID NO: 20 | Nuclease-capture aptamer GFP_3 nucleotide sequence |
| SEQ ID NO: 21 | Nuclease-capture aptamer GFP_4 nucleotide sequence |
| SEQ ID NO: 22 | Nuclease-capture aptamer GFP_5 nucleotide sequence |
| SEQ ID NO: 23 | Nuclease-capture aptamer GFP_6 nucleotide sequence |
| SEQ ID NO: 24 | Nuclease-capture aptamer GFP_7 nucleotide sequence |
| SEQ ID NO: 25 | Nuclease-capture aptamer GFP_8 nucleotide sequence |
| SEQ ID NO: 26 | Nuclease-capture aptamer GFP_9 nucleotide sequence |
| SEQ ID NO: 27 | Nuclease-capture aptamer GFP_10 nucleotide sequence |
| SEQ ID NO: 28 | Nuclease-capture aptamer GFP_11 nucleotide sequence |
| SEQ ID NO: 29 | Nuclease-capture aptamer GFP_12 nucleotide sequence |
| SEQ ID NO: 30 | Nuclease-capture aptamer GFP_13 nucleotide sequence |
| SEQ ID NO: 31 | Nuclease-capture aptamer GFP_14 nucleotide sequence |
| SEQ ID NO: 32 | Nuclease-capture aptamer GFP_15 nucleotide sequence |
| SEQ ID NO: 33 | Nuclease-capture aptamer GFP_16 nucleotide sequence |
| SEQ ID NO: 34 | Nuclease-capture aptamer GFP_17 nucleotide sequence |
| SEQ ID NO: 35 | Nuclease-capture aptamer GFP_18 nucleotide sequence |
| SEQ ID NO: 36 | Nuclease-capture aptamer GFP_19 nucleotide sequence |
| SEQ ID NO: 37 | Nuclease-capture aptamer GFP_20 nucleotide sequence |
| SEQ ID NO: 38 | Nuclease-capture aptamer GFP_21 nucleotide sequence |
| SEQ ID NO: 39 | Nuclease-capture aptamer GFP_22 nucleotide sequence |
| SEQ ID NO: 40 | Nuclease-capture aptamer GFP_23 nucleotide sequence |
| SEQ ID NO: 41 | Nuclease-capture aptamer GFP_24 nucleotide sequence |
| SEQ ID NO: 42 | Poly-A tail nuclease-capture aptamer GFP_25 nucleotide sequence |
| SEQ ID NO: 43 | Nuclease-capture aptamer Hyg_4 nucleotide sequence |
| SEQ ID NO: 44 | Nuclease-capture aptamer Hyg_5 nucleotide sequence |
| SEQ ID NO: 45 | Nuclease-capture aptamer Hyg_6 nucleotide sequence |
| SEQ ID NO: 46 | Nuclease-capture aptamer Hyg_7 nucleotide sequence |
| SEQ ID NO: 47 | Nuclease-capture aptamer Hyg_8 nucleotide sequence |
| SEQ ID NO: 48 | Nuclease-capture aptamer Hyg_9 nucleotide sequence |
| SEQ ID NO: 49 | Nuclease-capture aptamer Hyg_10 nucleotide sequence |
| SEQ ID NO: 50 | Nuclease-capture aptamer Hyg_11 nucleotide sequence |
| SEQ ID NO: 51 | Nuclease-capture aptamer Hyg_12 nucleotide sequence |
| SEQ ID NO: 52 | Nuclease-capture aptamer Hyg_13 nucleotide sequence |
| SEQ ID NO: 53 | Nuclease-capture aptamer Hyg_14 nucleotide sequence |
| SEQ ID NO: 54 | Nuclease-capture aptamer Hyg_15 nucleotide sequence |
| SEQ ID NO: 55 | Nuclease-capture aptamer Hyg_16 nucleotide sequence |
| SEQ ID NO: 56 | Nuclease-capture aptamer Hyg_17 nucleotide sequence |
| SEQ ID NO: 57 | Nuclease-capture aptamer Hyg_18 nucleotide sequence |

TABLE 1-continued

Summary of Sequence Identifiers

| Sequence Identifier | Sequence |
|---|---|
| SEQ ID NO: 58 | Nuclease-capture aptamer Hyg_19 nucleotide sequence |
| SEQ ID NO: 59 | Nuclease-capture aptamer Hyg_20 nucleotide sequence |
| SEQ ID NO: 60 | Nuclease-capture aptamer Hyg_21 nucleotide sequence |
| SEQ ID NO: 61 | Nuclease-capture aptamer Hyg_22 nucleotide sequence |
| SEQ ID NO: 62 | Nuclease-capture aptamer Hyg_23 nucleotide sequence |
| SEQ ID NO: 63 | Nuclease-capture aptamer Hyg_24 nucleotide sequence |
| SEQ ID NO: 64 | Nuclease-capture aptamer Hyg_25 nucleotide sequence |
| SEQ ID NO: 65 | Nuclease-capture aptamer Hyg_26 nucleotide sequence |
| SEQ ID NO: 66 | Nuclease-capture aptamer Hyg_27 nucleotide sequence |
| SEQ ID NO: 67 | Nuclease-capture aptamer Hyg_28 nucleotide sequence |
| SEQ ID NO: 68 | Nuclease-capture aptamer Hyg_29 nucleotide sequence |
| SEQ ID NO: 69 | Nuclease-capture aptamer Hyg_30 nucleotide sequence |
| SEQ ID NO: 70 | Nuclease-capture aptamer Hyg_31 nucleotide sequence |
| SEQ ID NO: 71 | Nuclease-capture aptamer Hyg_32 nucleotide sequence |
| SEQ ID NO: 72 | Nuclease-capture aptamer Hyg_33 nucleotide sequence |
| SEQ ID NO: 73 | Nuclease-capture aptamer Hyg_34 nucleotide sequence |
| SEQ ID NO: 74 | Nuclease-capture aptamer Hyg_35 nucleotide sequence |
| SEQ ID NO: 75 | Nuclease-capture aptamer Hyg_36 nucleotide sequence |
| SEQ ID NO: 76 | Nuclease-capture aptamer Hyg_37 nucleotide sequence |
| SEQ ID NO: 77 | Nuclease-capture aptamer Hyg_38 nucleotide sequence |
| SEQ ID NO: 78 | Nuclease-capture aptamer Hyg_39 nucleotide sequence |
| SEQ ID NO: 79 | Poly-A tail nuclease-capture aptamer Hyg_40 nucleotide sequence |
| SEQ ID NO: 80 | Amine-tagged version of the 18S rRNA probe nucleotide sequence |
| SEQ ID NO: 81 | Hygromycin 18S rRNA linker 1 nucleotide sequence |
| SEQ ID NO: 82 | Hygromycin 18S rRNA linker 2 nucleotide sequence |
| SEQ ID NO: 83 | Hygromycin 18S rRNA linker 3 nucleotide sequence |
| SEQ ID NO: 84 | Hygromycin 18S rRNA linker 4 nucleotide sequence |
| SEQ ID NO: 85 | Hygromycin 18S rRNA linker 5 nucleotide sequence |
| SEQ ID NO: 86 | Nuclease-capture aptamer 18S_4 nucleotide sequence |
| SEQ ID NO: 87 | Nuclease-capture aptamer 18S_5 nucleotide sequence |
| SEQ ID NO: 88 | Nuclease-capture aptamer 18S_6 nucleotide sequence |
| SEQ ID NO: 89 | Nuclease-capture aptamer 18S_7 nucleotide sequence |
| SEQ ID NO: 90 | Nuclease-capture aptamer 18S_8 nucleotide sequence |
| SEQ ID NO: 91 | Nuclease-capture aptamer 18S_9 nucleotide sequence |
| SEQ ID NO: 92 | Nuclease-capture aptamer 18S_10 nucleotide sequence |
| SEQ ID NO: 93 | Nuclease-capture aptamer 18S_11 nucleotide sequence |
| SEQ ID NO: 94 | Nuclease-capture aptamer 18S_12 nucleotide sequence |
| SEQ ID NO: 95 | Nuclease-capture aptamer 18S_13 nucleotide sequence |
| SEQ ID NO: 96 | 18S biotinylated capture probe nucleotide sequence |
| SEQ ID NO: 97 | 18S biotinylated capture aptamer nucleotide sequence |
| SEQ ID NO: 98 | EcoRI aptamer trigger nucleotide sequence |

In a first aspect, the present invention provides a method for detecting a target nucleic acid in a sample, the method comprising forming a reaction mix comprising:
 the sample;
 a nuclease;
 a solid substrate;
 a probe nucleic acid which is hybridisable under the conditions of the method to a first portion of the target nucleic acid, wherein the probe nucleic acid is immobilisable on the solid substrate; and
 a capture structure comprising a capture portion which is able to capture the nuclease and a targeting portion comprising a nucleotide sequence which is hybridisable under the conditions of the method to a second portion of the target nucleic acid;
 wherein the presence of the target nucleic acid in the sample allows the formation of a complex on the solid substrate wherein the complex comprises the probe nucleic acid, the target nucleic acid, the capture structure and a captured nuclease; and
 determining the extent of complex formation, wherein the extent of complex formation is positively correlated with the presence of the target nucleic acid in the sample.

As set out above, the present invention contemplates forming a reaction mix comprising a sample; a nuclease; a solid substrate; a probe nucleic acid; and a capture structure. One or more components of the reaction mix may be mixed together, or may be added in sequentially. Where components of the reaction mix are added sequentially, wash steps may be used between the addition of one or more components. Typically, the purpose of such wash steps is to remove components from the reaction mix that are not bound to the solid support either directly in the case of the probe nucleic acid or indirectly via one or more other components of the reaction mix or complex.

A range of suitable wash buffers or solutions would be ascertainable by a person skilled in the art. Washes may also be conducted under any suitable temperatures and, in some embodiments, washes at ambient or room temperature have been found to be suitable.

For example, in some embodiments, the probe nucleic acid and solid substrate may be mixed or conjugated prior to the addition of the other components such that the probe nucleic acid is pre-immobilised onto the solid substrate prior to contact with the other components of the reaction mix.

Also, in some embodiments, the nuclease may be added to the reaction mix after the formation of the remainder of the complex. In these embodiments, a wash step may be used between formation of the remainder of the complex and the addition of the nuclease. The purpose of this wash step would be to remove any components of the reaction mix that are not incorporated into the complex.

The methods of the present invention may be used to detect any suitable nucleic acid target. As such, target nucleic acids may include, for example, DNA or RNA. In some embodiments, the target nucleic acid is RNA such as mRNA or rRNA. Typically, the target nucleic acid is in a single-stranded state at least when contacted with the probe nucleic acid and the capture structure. As such, in some embodiments the target nucleic acid may comprise a single stranded nucleic acid. The target nucleic acid may also be a single stranded nucleic acid formed by denaturation of a double stranded nucleic acid molecule.

The "sample" in which a target may be detected may be any sample that putatively contains the target. For example, the sample may be a biological sample including samples derived from an organism, a sample containing one or more cells, tissue samples, organ samples, a blood sample, a plasma sample, a CSF fluid sample, an amniotic fluid sample and the like; an environmental sample such as a water, air or soil sample; a food or beverage sample; and the like. The samples contemplated herein may be used in a crude form, or the samples may be processed for use in accordance with the present invention. For example, the sample may have one or more extraction or purification steps performed thereon in order to purify or semi-purify the target present in the sample.

As set out above, the present invention contemplates the use of a nuclease.

As referred to herein, a "nuclease" should be understood as any enzyme that can cleave the sugar-phosphate backbone of a nucleic acid. As such, the term "nuclease" should be understood to encompass both endonucleases and exonucleases. Furthermore, the nucleases contemplated for use in accordance with the present invention may be deoxyribonucleases (which cleave DNA) or ribonucleases (which cleave RNA). In some embodiments, the nuclease used in accordance with the present invention is a nuclease that cannot cleave or digest the target or other components of the reaction mix, but which can cleave or digest another nucleotide sequence, such as a reporter nucleotide sequence (see later) such that the activity of the nuclease may be detected. Nucleases that may be used in accordance with the present invention include, for example, restriction endonucleases, nucleases that cleave at sequence mis-matches, S1 nuclease, T7 endonuclease I, T4 endonuclease VII, CEL I (a plant-specific extracellular glycoprotein that belongs to the S1 nuclease family), and ribonucleases such as RNase A or RNase H.

As set out above, in some embodiments, the nuclease may be a restriction endonuclease. As referred to herein, a "restriction endonuclease" refers to any endonuclease that binds to double-stranded DNA at a specific nucleotide sequence and then, if both strands of the DNA lack appropriate modification at that sequence, cleaves the DNA either at the recognition sequence or at another site in the DNA molecule. A wide array of restriction endonucleases with different recognition sites and different cleavage sites would be readily ascertained by one of skill in the art. For example, a range of restriction endonucleases may be sourced from New England Biolabs (Ipswich, Mass., USA).

In some embodiments, the restriction endonuclease may be EcoRI.

In some embodiments, the nuclease used in accordance with the present invention is an RNase.

In some embodiments the RNase is an RNase H. RNase H (EC 3.1.26.4) is a ribonuclease that cleaves the 3'-O—P-bond of RNA in a DNA/RNA duplex to produce 3'-hydroxyl and 5'-phosphate terminated products. RNase H is a non-specific endonuclease and catalyzes the cleavage of RNA via a hydrolytic mechanism, aided by an enzyme-bound divalent metal ion.

In some embodiments, the RNase is an RNase A. Reference herein to an "RNase A" should be understood as any endonuclease which cleaves single stranded RNA. Examples of RNase A are described under EC 3.1.27.5. In these embodiments, the activity of the nuclease would typically be detected by detecting digestion of an RNA substrate. In some embodiments, RNase A might be a suitable nuclease wherein the target nucleic acid, the probe nucleotide sequence and the capture structure comprise DNA.

As set out above, the method comprises providing a "solid substrate" on which the complex may form in the presence of the target nucleic acid. The solid substrate may be any suitable substrate for binding the probe nucleic acid and formation of the complex on the solid substrate. The solid substrate may, for example, comprise a surface of a multi-well plate (e.g. an ELISA plate), a multi-well strip, a bead, a dip stick, a microfluidic device, array chip, etc.

In some embodiments, the solid substrate may also comprise a substance that promotes binding of the probe nucleic acid or may be treated to promote binding of the probe nucleic acid. In some embodiments, the solid substrate may comprise a plastic substrate including, for example, polystyrene, polyvinyl chloride or cyclo-olefin. In some embodiments, the solid substrate may be transparent or coloured depending whether the detection method involves a colourimetric, fluorescence or other read out.

In some embodiments, the solid substrate may also be treated to increase the binding affinity of the probe nucleic acid to the solid substrate. For example, the solid substrate may be irradiated or functionalised to allow covalent bonding between the substrate and the probe nucleic acid. As set out below, the solid substrate may also be functionalised with a ligand for the probe nucleic acid.

As set out above, the present invention also contemplates a "probe nucleic acid". The probe nucleic acid is hybridisable under the conditions of the method to a first portion of the target nucleic acid, and the probe nucleic acid is also immobilisable on the solid substrate.

Immobilisation of the probe nucleic acid to the solid substrate may occur through covalent bonding of the probe to the solid substrate or immobilization may occur via ligands on the probe nucleic acid and the solid substrate. As can be appreciated, a range of different ligand binding pairs may be used. In some embodiments, the ligands may be interchangeable between the probe nucleic acid and the solid substrate.

In some embodiments, the ligand binding pairs include biotin and avidin or streptavidin (or derivates thereof). Derivatives of avidin or streptavidin are known in the art and may include forms of avidin or streptavidin that have been modified to increase their binding affinity to modified and/or unmodified solid substrates or ligands. For example, streptavidin may be modified to add amine groups, histidine residues or sulfhydryl groups to the molecule. In some embodiments, the derivative of streptavidin may comprise neutravidin, captavidin or streptavidin mutants (e.g. H127C or S139C).

In some embodiments, hydrophobic or hydrophilic ligands may be passively bound to hydrophobic or hydrophilic solid substrates, respectively. For example, streptavidin (or derivates thereof) may be passively bound to hydrophobic solid substrates. In some embodiments, the solid substrate may comprise a linker which facilitates covalent bonding of the ligand to the solid substrate. For example, the linker may comprise glutathione, maleic anhydride, a metal chelate, or maleimide. The ligand may then be bound to the solid substrate via the linker.

The probe nucleic acid may be immobilized onto the solid substrate prior to formation of the reaction mix, or the probe may immobilise onto the solid substrate in the presence of one or more other components of the reaction mix.

As set out above, the present invention also contemplates the use of a "capture structure" comprising a capture portion which is able to capture a nuclease and a targeting portion comprising a nucleic acid which is hybridisable under the conditions of the method to a second portion of the target nucleic acid.

The "capture portion" of the capture structure may be any agent which is able to at least bind to and, optionally, inhibit the activity of a nuclease.

In some embodiments, the capture portion of the capture structure comprises an aptamer.

The term "aptamer", as referred to herein, should be understood as a nucleic acid molecule, at least a portion of which is able to bind to another molecule. Nucleic acid aptamers are generally single-stranded nucleic acid molecules with complex secondary or tertiary structures (which may include double-stranded portions or regions) that can specifically bind a target molecule with high affinity. When bound to enzymes, certain aptamers are able to reduce or inhibit their enzymatic activity. Generally, the aptamers contemplated by the present invention can at least bind to a nuclease. Furthermore, in some embodiments, the nuclease-binding aptamers contemplated by the present invention may reduce or eliminate the activity of the nuclease when bound thereto. The aptamers of the present invention may also comprise a region which does not bind to the nuclease. This region, or the nuclease-binding capture portion itself, may also exhibit binding affinity toward another molecule such as a target (e.g. a targeting portion, as described later).

The aptamers contemplated for use in accordance with the present invention may comprise any suitable nucleic acid or equivalent thereof. In this regard, the aptamers may comprise, for example, DNA, RNA, a nucleic acid mimic such as Peptide Nucleic Acid (PNA) or Locked Nucleic Acid (LNA), DNA or RNA comprising one or more modified nucleotides, and the like. "Modified" nucleotides include, for example, nucleotides having chemical modifications to any of the phosphate backbone, sugar moiety or base moiety of the nucleotide, tritylated bases and unusual bases such as inosine. The use of modified nucleotides may also affect the binding characteristics of the aptamer to the nuclease, for example as described in Latham et al. (*Nucl. Acids Res.* 22(14): 2817-2822, 1994).

In some embodiments RNA aptamers may be used, since RNA can form secondary structures that DNA generally does not, such as pseudoknots and base triples.

Nucleic acid aptamers may also be modified, for example to increase stability, in a number of ways including, for example:
 (i) Synthesis of aptamers using L-nucleotides (the mirror image of natural nucleotides) so that they cannot be degraded by naturally occurring nucleases;
 (ii) Incorporation of locked nucleic acid (LNA) and/or peptide nucleic acid (PNA) residues into the aptamer. LNAs and PNAs also increase stability of nucleic acid duplexes;
 (iii) Other chemical modifications of ribonucleotides, such as 2'-amino- and 2'-fluoro-pyrimidine nucleotides or 2'-O-methyl nucleotides; and/or
 (iv) Capping at the 3' end with a deoxythymidine to increase resistance to exonuclease degradation.

Nucleic acid aptamers that bind to, and inhibit the activity of, a particular protein (such as a nuclease) may be produced using methods known in the art. For example, in-vitro selection methods (e.g. see Ellington and Szostak, *Nature* 346 (6287): 818-22, 1990) and SELEX methods (e.g. see Tuerk and Gold, *Science* 249(4968): 505-510, 1990) may be used. Further details relating to the production and selection of aptamers may also be found in the review of Osborne and Ellington (*Chem. Rev.* 97(2): 349-370, 1997).

In some embodiments, the aptamer contemplated for use in the present methods may bind to and, optionally inhibit the activity of a nuclease, restriction endonuclease, RNase, RNase H or RNase A as hereinbefore defined.

In some embodiments wherein the nuclease is the restriction nuclease, EcoRI, the aptamer may include an aptamer as described in WO 2008/122088, the content of which is hereby incorporated by reference.

As set out above, the capture structures contemplated for use in the present invention also comprise a targeting portion. The "targeting portion" of the capture structure may be any nucleotide sequence which is hybridisable under the conditions of the method to a second portion of the target nucleic acid. In some embodiments where the capture portion of the capture structure is a nucleic acid (such as an aptamer) the capture portion and targeting portion may be regions of nucleotide sequence in a nucleic acid molecule.

As set out above, in the methods of the present invention, the presence of the target nucleic acid in the sample allows the formation of a complex on the solid substrate wherein the complex comprises the probe nucleic acid, the target nucleic acid, the capture structure and the nuclease.

In some embodiments, the complex formed between the probe, the target and the capture structure may comprise a plurality of capture portions and, thus, each target molecule may lead to the capture of multiple nuclease molecules.

In some embodiments, the complex may comprise a plurality of capture portions as a result of multiple capture structures binding to the target nucleic acid. In these embodiments, the multiple capture structures may bind to the target nucleic acid at multiple positions on the target nucleic acid.

In some embodiments wherein the complex comprises a plurality of capture portions, the capture structure further comprises a scaffold to which a plurality of capture portions can bind.

The "scaffold" may include any structure which is attachable to a targeting portion and to which a plurality of capture portions can bind.

For example, in some embodiments, the scaffold may comprise a nucleotide sequence to which a plurality of nuclease-capturing aptamers may hybridise.

In some embodiments, the scaffold may be a nucleic acid which is added to the reaction mix, such as a synthetic nucleic acid. In these embodiments, the targeting portion may comprise a region of nucleotide sequence within the scaffold itself, or the targeting portion may comprise a discreet linker nucleic acid which is able to hybridise to both the target nucleic acid and the scaffold nucleic acid.

In some embodiments, the scaffold may also comprise a nucleic acid which may be present in the sample. For example in some embodiments, the scaffold may comprise a ribosomal RNA (rRNA) which may be present in the sample. For eukaryotic-derived samples, a suitable rRNAs may include 18S rRNA, 5S rRNA, 28S rRNA and 5.8S rRNA. For prokaryotic-derived samples, suitable rRNAs may include the 16S rRNA, 5S rRNA and 23S rRNA. In some embodiments, the rRNA is a small-subunit rRNA such as 18S rRNA or 16S rRNA.

In these embodiments, a plurality of capture portions may bind to the rRNA scaffold nucleic acid, while the targeting portion comprises a linker nucleotide sequence which links the rRNA scaffold nucleic acid to the target nucleic acid. Thus, in these embodiments, the process of the re-designing individual nuclease-capture aptamers (and associated structure such as any helper oligonucleotides) with target binding moieties is avoided. Rather, target specificity may be conferred by designing only a linker nucleotide sequence which links a target nucleic acid to an rRNA scaffold.

In some embodiments, the scaffold may also comprise a solid substrate attached to a targeting portion wherein a plurality of capture portions can bind to the scaffold. Examples of suitable solid substrate scaffolds include, for example various beads or other particles known in the art to which a nucleic acid may be attached.

In some embodiments, the method of the present invention may further comprise the addition of one or more helper oligonucleotides to the reaction mix wherein the one or more helper oligonucleotides bind to the target nucleic acid at a site adjacent to the binding site of the probe nucleic acid and/or a capture structure.

Helper oligonucleotides serve to reduce secondary structure in a target nucleotide sequence in a region surrounding the binding site of the probe nucleic acid and/or a capture structure by binding to the target nucleic acid at a site adjacent to the binding site of the probe nucleic acid and/or a capture structure. As such, a helper oligonucleotide can reduce steric hindrance between the target nucleic acid and the probe nucleic acid and/or a capture structure and thus improve the sensitivity and/or efficiency of the method. Helper oligonucleotides are further described in detail by Barken et al. (*Biotechniques* 1: 124-132, 2004).

Binding of a helper oligonucleotide at a site "adjacent" to the binding site of the probe nucleic acid and/or a capture structure generally refers to a separation of less than 10, less than 5 or about 3 nucleotide residues between the binding site of the helper oligonucleotide and the binding site of the of the probe nucleic acid and/or a capture structure. The binding site of the helper oligonucleotide may be 3' and/or 5' of the binding site of the probe nucleic acid and/or a capture structure on the target nucleic acid.

In some embodiments, the probe nucleic acid and/or one or more capture structures may also function as helper oligonucleotides with respect to each other wherein one or more of these components bind adjacent to each other.

As set out above, the method of the present invention involves determining the extent of complex formation, wherein the extent of complex formation is positively correlated with the presence of the target nucleic acid in the sample.

In some embodiments, determining the extent of complex formation comprises measuring a residual nuclease activity in the reaction mix, wherein the extent of the residual nuclease activity is negatively correlated with the extent of complex formation.

Generally, "residual nuclease activity" in the reaction mix is the level of nuclease activity in the reaction mix as measured after inhibition of the nuclease by the aptamer in the complex and/or separation of the solid support comprising the bound complex from the remainder of the reaction mix.

In some embodiments, in order to measure residual nuclease activity, the solid substrate, probe nucleic acid, target nucleic acid and capture structure are allowed to form a complex prior to the addition of the nuclease to the reaction mix. A wash step may then also be used to remove the above components which are not incorporated into the complex. After the wash step, a nuclease may then added in solution, and the amount of nuclease captured into the complex is dependent upon the amount of capture structure that is immobilized to the solid substrate, which is in turn dependent on the amount of target nucleic acid initially present. The residual nuclease activity may then be measured in solution after capture and inhibition of the nuclease in the complex or at least capture of the nuclease in the complex followed by removal of the complex from the solution (e.g. by removal of the solid substrate comprising the bound complex). In some embodiments, residual nuclease activity is measured relative to a control in which the target is known to be absent and thus the residual nuclease activity in the solution should be not substantially reduced relative to the amount of nuclease added. In this way, residual nuclease activity for a sample may be expressed as a reduction in nuclease activity relative to the nuclease activity in the control.

In some embodiments, determining the extent of complex formation may also comprise measuring a nuclease activity associated with the complex, wherein the extent of nuclease activity associated with the complex is positively correlated with the extent of complex formation.

In some embodiments, determining the extent of complex formation comprises measuring a nuclease activity associated with the complex after separation of the solid support comprising the complex from the remainder of the reaction mix.

In some embodiments in order to determine the nuclease activity associated with the complex, the method further comprises displacement of the nuclease from the complex and measurement of the displaced nuclease activity.

In order to release a nuclease from aptamer mediated inhibition, an aptamer that is amenable to denaturation by the addition of an oligonucleotide trigger can be incorporated into the capture structure. Following complex formation and the removal non-captured nuclease molecules, the addition of a trigger nucleic acid can disrupt the aptamer's secondary structure and release the nuclease from inhibition. The activity of the nuclease may then be detected.

In some embodiments wherein the nuclease comprises EcoRI, a suitable oligonucleotide trigger may comprise the nucleotide sequence GTTGAACTCGTCTTG (SEQ ID NO: 98).

The conditions required for an oligonucleotide trigger to release a nuclease from inhibition would be readily ascertained by those skilled in the art. In some embodiments, the conditions include a temperature of at least about 20° C. as temperatures substantially below this lead to the aptamer being too stable to be disrupted by the oligonucleotide trigger.

The method used for detecting the activity of the nuclease may be any suitable method for the subject nuclease. In some embodiments, the activity of the nuclease is determined by the rate or extent of digestion of a reporter nucleotide sequence.

For example, the activity of a DNase or RNase may be ascertained by observing degradation, cleavage or digestion of a reporter nucleotide sequence comprising DNA or an analog thereof, RNA or an analog thereof or both DNA or an analog thereof and RNA or an analog thereof.

The reporter nucleotide sequence may be single-stranded or double-stranded, as appropriate for the activity of the nuclease. Cleavage of the reporter nucleotide sequence may be detected by any known method. For example, cleavage of a reporter nucleotide sequence into a lower molecular weight product may be determined by electrophoretic methods, staining methods, the release of a labelled nucleotide, cleavage of a fluorophore/quencher labelled nucleic acid to release a fluorophore, and the like.

In some embodiments, a fluorophore is bound to the reporter nucleotide sequence and a quencher, which quenches the fluorescence of the fluorophore, is also bound to the reporter nucleotide sequence, wherein digestion of all or part of the reporter nucleotide sequence reduces or eliminates the quenching of the fluorophore by the quencher.

Exemplary fluorophores and quenchers would be readily ascertained by one of skill in the art. In this regard, reference is made to the review of Marras (*Methods Mol. Biol.* 335: 3-16, 2006).

In embodiments utilising a restriction endonuclease, the activity of the restriction endonuclease may be determined by the rate or extent of cleavage of a reporter nucleotide sequence which comprises at least a region of double stranded DNA.

In embodiments utilising an RNase H, the activity of the RNase H may be determined by the rate or extent of cleavage of a reporter nucleotide sequence which comprises a DNA/RNA duplex.

In embodiments utilising an RNase A, the activity of the RNase A may be determined by the rate or extent of cleavage of a reporter nucleotide sequence which comprises ssRNA.

In the above embodiments, digestion of part of the reporter nucleotide sequence allows dissociation of the fluorophore and quencher and thus allows the generation of a signal by the fluorophore.

In some embodiments, the reporter nucleotide sequence is comprised within a Molecular Break-Light nucleic acid molecule as described by Biggins et al. (*Proc Natl. Acad. Sci. USA* 97(25): 13537-13542, 2000).

In some embodiments, a polypeptide may be bound to the reporter nucleotide sequence and an immobilisable agent may be bound to the reporter nucleotide sequence, wherein cleavage of the reporter nucleotide sequence releases the polypeptide from the immobilisable agent; such that after cleavage of the reporter nucleotide sequence and immobilisation of the immobilisable agent, the amount of non-immobilised polypeptide is indicative of the activity of the nuclease.

A wide array of "immobilisable agents" would be readily ascertained by one of skill in the art and may include, for example:
  (i) an antigen, which may be immobilised by contacting with an immobilised antibody that can bind the antigen;
  (ii) an antibody, which may be immobilised by contacting with an immobilised antigen or anti-idiotypic antibody that can bind the antibody;
  (iii) a polypeptide comprising a histidine tag, which may be immobilised by contacting an affinity medium comprising nickel or cobalt ions;
  (iv) biotin, which may be immobilised by contacting with immobilised avidin or streptavidin;
  (v) avidin or streptavidin, which may be immobilised by contacting with immobilised biotin; and/or
  (vi) a magnetic or paramagnetic particle, which may be immobilised via a magnetic field.

As set out above, some immobilisable agents may be immobilised by contacting the immobilisable agent with a binding partner that is itself immobilised. The immobilisation of the binding partner may be achieved using any means known in the art. For example, the binding partner of the immobilisable agent may be immobilised onto a surface of a culture vessel, tube or plate (which may have been pre-treated with an agent such as a silane), immobilised onto the surface of a bead or other particle, immobilised onto a column or other chromatography medium, immobilised onto a membrane, or immobilised onto a solid substrate suitable for an array.

A range of other immobilisable agents would also be readily ascertained by one of skill in the art, and the present invention should not be considered in any way limited to the immobilisable agents exemplified above.

After immobilisation of the immobilisable agent, any polypeptide remaining "free" in the sample may be detected using any standard methods of protein detection, as are known in the art such as electrophoresis, immunochromatographic tests, including lateral flow strips, western blotting, mass spectroscopy, detection using a biosensor (for a review of biosensor-based detection of proteins in solution see Leca-Bouvier and Blum, *Analytical Letters* 38(10): 1491-1517, 2005). A range of exemplary protein detection methods may be found in *Proteins and Proteomics: A Laboratory Manual* (Simpson, CSHL Press, 2003).

In the case of polypeptides with detectable activity, such as enzymatic activity, the polypeptide may be detected by detection of the activity of the polypeptide. Suitable polypeptides with detectable enzymatic activity may include, for example, peroxidases such as HRP, glucorinidases such as GUS and galactosidases such as beta-galactosidases.

In a second aspect, the present invention also provides a kit for performing the method of the first aspect of the invention, the kit comprising:
  a nuclease;
  a solid substrate;
  a probe nucleic acid which is hybridisable to a first portion of a target nucleic acid, wherein the probe nucleic acid is immobilisable on the solid substrate; and
  a capture structure comprising a capture portion which is able to capture the nuclease and a targeting portion comprising a nucleotide sequence which is hybridisable to a second portion of a target nucleic acid.

In some embodiments, the nuclease, solid substrate, probe nucleic acid and capture structure in the kit may be as hereinbefore described with reference to the first aspect of the invention.

In addition, the kit according to the second aspect of the invention may also comprise one more additional reagents needed to perform the method of the first aspect of the invention. Instructions for performing the method, and/or suitable reaction vessels may also be included in the kit.

Finally, reference is made to standard textbooks of molecular biology that contain methods for carrying out basic techniques encompassed by the present invention, including DNA restriction and ligation for the generation of the various genetic constructs described herein. See, for example, Maniatis et al., *Molecular Cloning: A Laboratory Manual* (Cold Spring Harbor Laboratory Press, New York, 1982) and Sambrook et al. (2000, supra).

The present invention is further described by the following non-limiting examples. It is to be understood that the following description is for the purpose of describing particular embodiments only and is not intended to be limiting with respect to the above description.

EXAMPLE 1

Target Nucleic Acid-Mediated Capture of a Nuclease

In some embodiments, the method of the present invention generates a detectable signal via a target nucleic acid-mediated capture of a nuclease molecule.

In these embodiments, following target nucleic acid-mediated nuclease capture, signal transduction can occur by way of two mechanisms:
  the removal of a nuclease from solution or the inhibition of a captured nuclease's activity can generate a signal via a reduction in active nuclease molecules in solution relative to a no-target control; and/or
  a captured nuclease can generate a signal through its activity upon release from capture.

The measurement of the activity of the nuclease molecules present in solution via detection of the cleavage of their substrate signaling molecules constitutes the signal generation mechanism of the present invention.

Target-specific nuclease capture is based on the formation of a complex between a nuclease and three discrete components:
  a probe nucleic acid which is hybridisable under the conditions of the method to a first portion of the target nucleic acid, wherein the probe nucleic acid is immobilisable on the solid substrate. Immobilisation may occur through covalent bonding to the solid substrate or via ligands on the probe nucleic acid and the substrate. For example, in some embodiments, the probe nucleic acid may be biotinylated and the solid substrate may comprise bound avidin or streptavidin. The solid substrate may be any suitable substrate such as a microtitre well, a microsphere, a dipstick or the like;
  a target nucleic acid, which may be DNA or RNA, in a single-stranded state; and
  a capture structure comprising a capture portion which is able to capture a nuclease and a targeting portion comprising a nucleic acid which is hybridisable under the conditions of the method to a portion of the target nucleic acid.

In the presence of the target nucleic acid, a complex is formed (and immobilized) on the solid substrate, the complex comprising the probe, the target nucleic acid and the capture structure. The immobilised complex may then be retained on the solid substrate through wash treatments, while capture structures not bound to the target nucleic acid are removed. Thus, the retention of the capture structure is dependent on the presence of the target nucleic acid.

Target specificity of the method can be achieved either through the specific binding of the probe to the target, specific binding of the capture structure to the target, or both.

To improve immobilisation of the target on a solid surface, multiple probes can be utilised to bind to different portions of a nucleic acid target (e.g. see Flagella et al., Anal. Biochem. 352(1): 50-60, 2006). In addition, helper oligonucleotides which bind to the 5' and 3' regions adjacent to the probe- and capture structure-binding sites on the target nucleic acid can be used to reduce steric hindrance and increase sensitivity (e.g. see Barken et al., 2004, supra).

One method of capturing a nuclease molecule is by means of a nucleic acid aptamer. Aptamers are nucleic acids with complex structures that can bind strongly and specifically to their target molecule. In addition, some aptamers can inhibit the enzymatic activity of nuclease targets. Appropriate nuclease-binding and nuclease-inhibiting aptamers for use in the capture structure may be selected using the SELEX procedure (see Tuerk and Gold, Science 249(4968): 505-510, 1990; and Ellington and Szostak, Nature 346(6287): 818-22, 1990).

Figure 1:
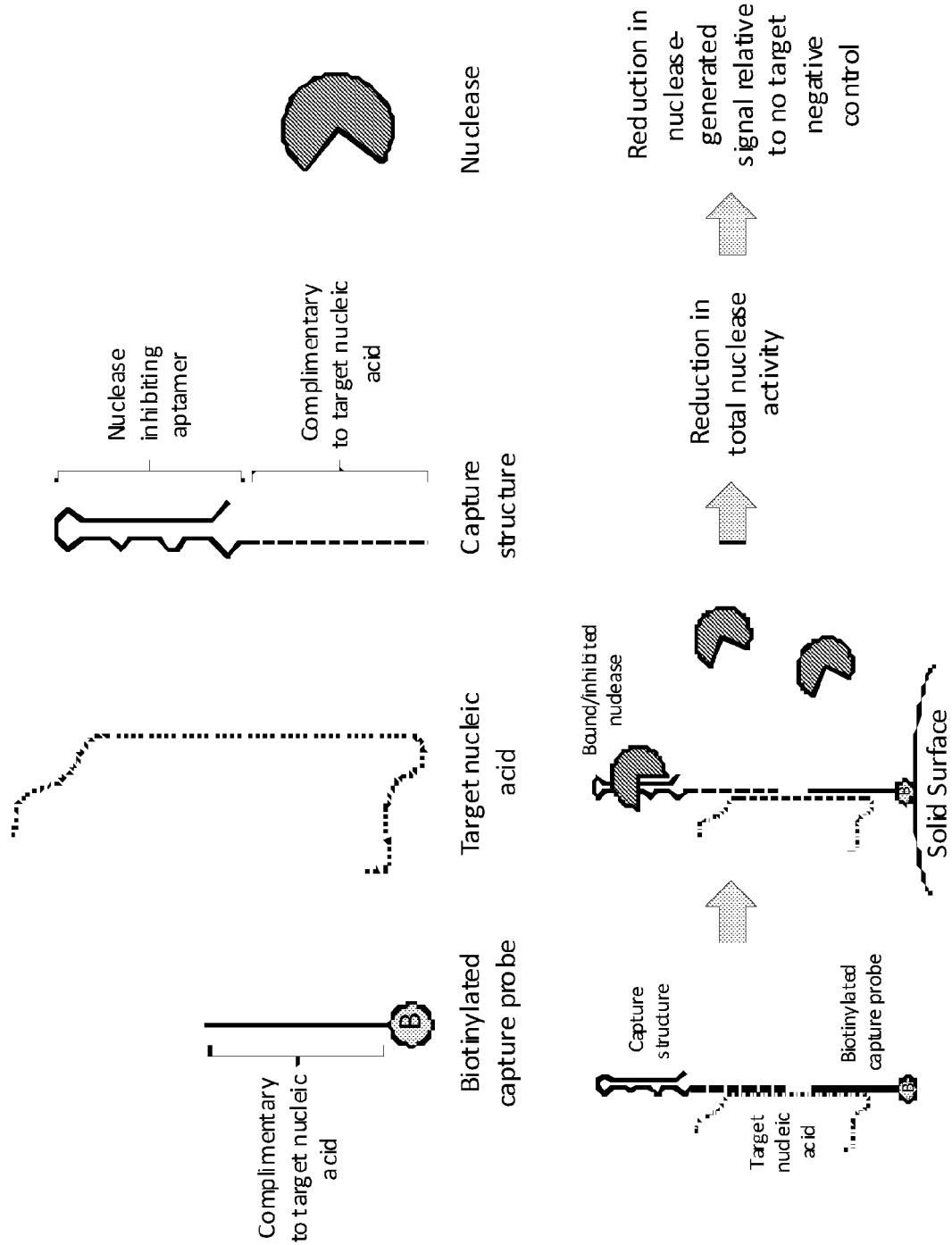
FIG. 1 illustrates an embodiment of the present invention wherein the presence of a target nucleic acid allows for co-purification of a capture structure and inhibition or removal of a nuclease. Three components of the complex include the probe, target nucleic acid and capture structure. The presence of a target nucleic acid allows a capture structure to be co-purified in a highly specific manner. The capture structure induces a reduction in nuclease activity relative to a no target control via inhibition or removal from solution of the nuclease, indicating the target nucleic acid was present in the original sample. The level of nuclease activity in the reaction may be indicated by the rate of nuclease-specific cleavage of substrate signaling molecules.

A schematic illustrating a first embodiment of the invention, in which a co-purified capture-structure aptamer can bind to and remove a nuclease molecule from solution, or inhibit its activity, is shown in FIG. 1.

The aptamer(s) used in the FIG. 1 embodiment should be structurally stable under a range of reaction conditions. A stable hairpin-like aptamer that binds to and inhibits the restriction endonuclease EcoRI was chosen to demonstrate this system. In this embodiment, the addition of a target-binding moiety to the aptamer's 5' or 3' terminus does not adversely impact on the aptamer's ability to bind to and strongly inhibit EcoRI, particularly at room temperature (~22° C.). Accordingly, the capture structure in its simplest form may be a single oligonucleotide comprising a target-binding portion and an EcoRI-binding binding portion.

Following the formation of a complex comprising the hybridised probe, the target nucleic acid and the capture structure, and removal of unbound capture structures via a wash step, the nuclease is added to the solution for aptamer-mediated capture.

Captured nuclease molecules can be subsequently removed from solution by purification or remain and be inhibited by the capture structure's aptamer. Nuclease activity in solution can then be determined by analysing the cleavage of substrate signaling molecules. In each instance, a reduction in total nuclease activity relative to a no-target negative control indicates the presence of the target nucleic acid in the original sample.

In some embodiments, it may be desirable to cleave the capture structure from the complex subsequent to the wash steps. For example, where the target nucleic acid is RNA and the captured nuclease is to be inhibited rather than removed, a ribonuclease such as RNase A can be used to digest the single-stranded target RNA portion of the complex. This allows for the separation of the capture structure from the remainder of the complex, i.e. the target and surface-bound probe. If the complex is retained on magnetic beads, the beads can be removed from solution to avoid adversely impacting the analysis of nuclease activity. In addition, any steric hindrance issues associated with access of the nuclease to the target-bound capture-structure will likely be reduced.

Figure 2:
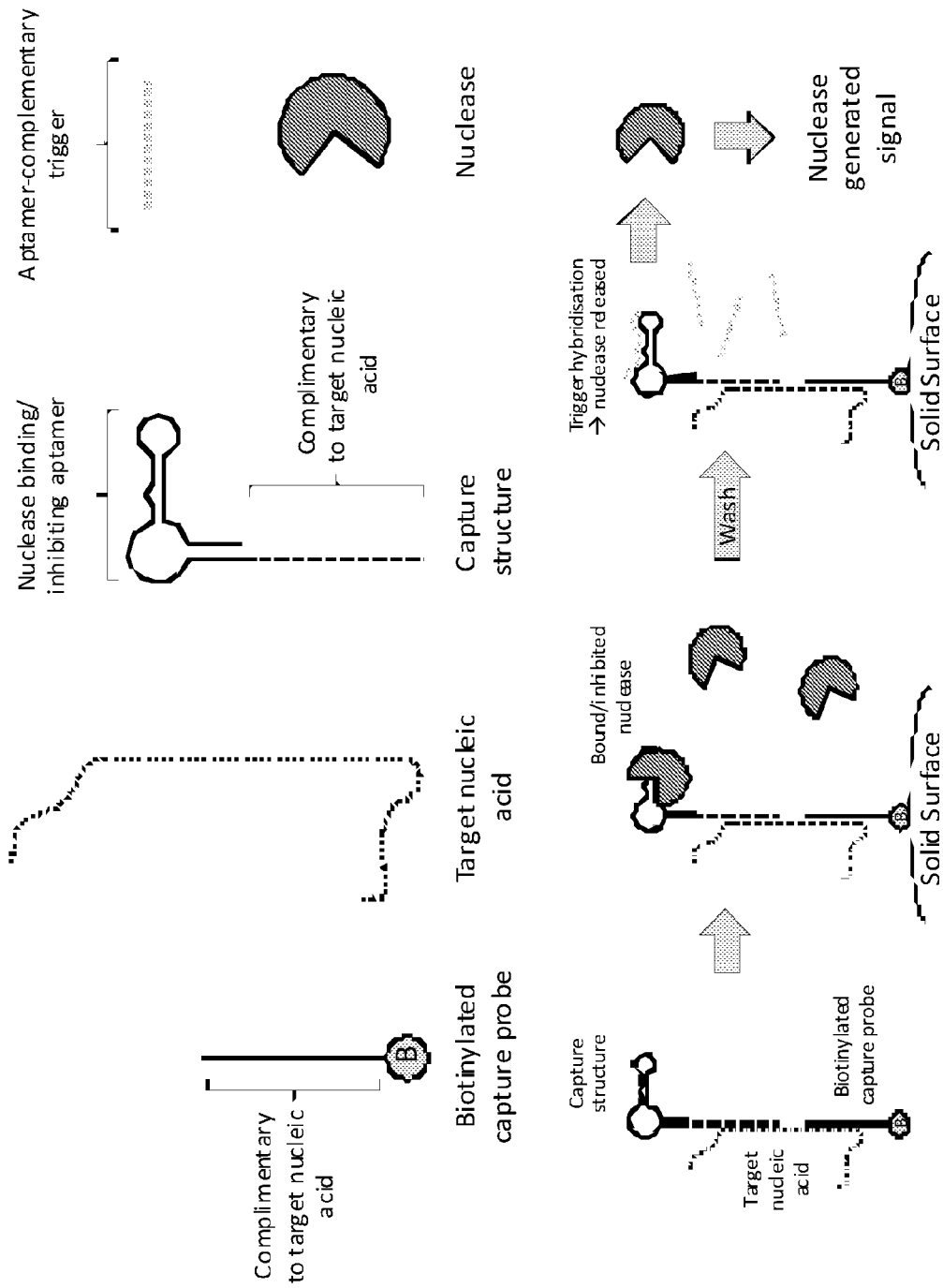
FIG. 2 illustrates an embodiment wherein the presence of the target nucleic acid allows for co-purification of a capture structure and release of a captured nuclease from inhibition. Three components of the complex include the capture probe, target nucleic acid and capture structure. The presence of a target nucleic acid allows the capture structure to be co-purified in a highly specific manner. Following nuclease capture and the removal of unbound nucleases from solution, a captured nuclease can be released from inhibition via the addition of an oligonucleotide trigger. The level of nuclease activity in solution may be indicated by the rate of nuclease-specific cleavage of a signaling molecule.

A schematic illustrating a second embodiment of the invention, in which a co-purified capture-structure can capture then release a nuclease molecule through the addition of a trigger oligonucleotide, is displayed in FIG. 2.

In the embodiment illustrated in FIG. 2, nuclease molecules captured in the complex can be released from inhibition in order to generate a signal.

In order to release a nuclease from aptamer mediated inhibition, an aptamer that is amenable to denaturation by the addition of an oligonucleotide trigger can be incorporated into the capture structure. Following complex formation and the removal of non-captured nuclease molecules, the addition of the trigger can disrupt the aptamer's secondary structure and release the nuclease from inhibition. The active nuclease is then able to cleave signaling molecules. The generation of a detectable signal by the cleavage of substrate signaling molecules by the nuclease indicates the presence of the target nucleic acid in the original sample.

A number of strategies also exist to enhance the sensitivity of the method of the present invention.

Figure 3:
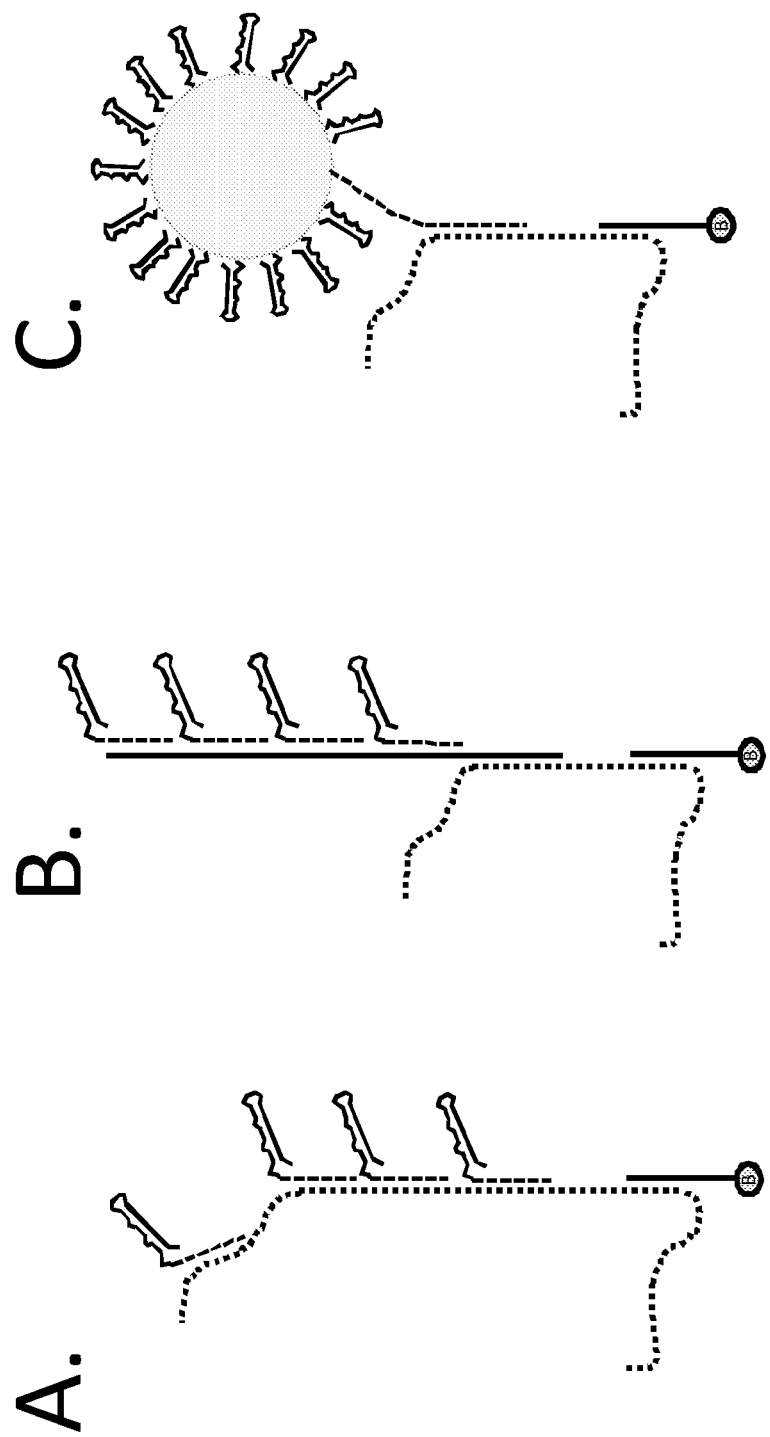
FIG. 3 illustrates embodiments of strategies for the capture of multiple nuclease molecules per target nucleic acid copy. Panel (A)—Multiple capture structures can bind to different regions within a target nucleic acid. Panel (B)—A single capture structure can consist of multiple aptamers hybridised to a nucleic acid scaffold. The scaffold possesses a targeting portion for hybridization to the target nucleic acid. Panel (C)—A single capture structure can also consist of multiple aptamers hybridised to a scaffold such as a nano-sphere. The scaffold in this embodiment comprises a hybridised target-complementary oligonucleotide for hybridization to the target nucleic acid.

In some embodiments, the capture structure may be constructed so that multiple aptamers are present for each target-binding moiety. In a further embodiment, multiple aptamers with different target binding sequences can bind to a single target at different positions. Furthermore, in embodiments where a target nucleic acid is an mRNA, multiple capture structures having poly-thiamine sequence can be used to bind to the mRNA's poly-adenosine tail. Examples of multiple binding and multi-aptamer capture structures are shown in FIG. 3. The aim of these strategies is to capture multiple nuclease molecules for each copy of the target nucleic acid. However, as the number of aptamers within each capture structure increases, the access of individual nuclease molecules is likely to decrease due to steric hindrance. As such, in some embodiments, aptamers may be separated from the capture structure following formation of the complex. Once free in solution the access of the aptamers to nuclease molecules in solution would be increased.

Various methods to release an aptamer from the complex would be readily ascertained by a person skilled in the art and may include, for example, nuclease digestion of linker portions, heat and chemical denaturation and the like.

In addition, in some embodiments, feedback strategies can be included to increase the number of active nuclease molecules present in solution. For example, where the method of the present invention incorporates measurement of an increase in nuclease activity (e.g. measurement of nuclease activity after capture of a nuclease in a complex followed by released of the nuclease) feedback strategies such as those described in WO 2009/152566 (the content of which is hereby incorporated by reference) may be employed.

Methods to detect the activity of a nuclease in the methods of the present invention can be adapted from those already described in the literature. For example, specific cleavage of fluorescent dual-labeled molecular break-lights containing the nuclease's recognition sequence (Biggins et al., Proc. Natl. Acad. Sci. USA 97(25): 13537-13542, 2000). To further increase sensitivity, nuclease-mediated cleavage of surface-tethered quantum dots or fluorescent nanospheres can be employed.

EXAMPLE 2

Detection of ssDNA (Hygromycin Resistance Gene)

For the generation of single-stranded DNA (ssDNA) target molecules, a 703 bp fragment of the hygromycin resistance gene, commonly present in genetically-modified plants, was amplified via standard PCR. Following gel-purification, the PCR product was used in asymmetric PCR reactions containing only the forward primer. Twenty-two cycles of linear amplification produced approximately 45 fmoles ssDNA/µl.

Oligonucleotides were designed to bind specifically to the ssDNA hygromycin target sequence and include:
a dual-biotinylated probe nucleic acid (dual biotin-CAT-CATCGAAATTGCCGTCAACCAAGCTCTGATAG; SEQ ID NO: 1);
two helper oligonucleotides:

```
Helper 1 (TGGTCAAGACCAATGCGGAGC; SEQ ID NO: 2);
and

Helper 2 (TCGCATCGACCCTGCGCCCAAG; SEQ ID NO: 3)
``` which bind adjacent to the probe; and
three capture structure nucleic acids comprising nuclease-capture aptamers with target-binding portions:

```
Nuclease-capture aptamer Hyg_1
(AGTCGTGGCGATCCTGCAAGCTCCGTACCGAATCGAAAACGAGTTCAAGG

TAC; SEQ ID NO: 4),

Nuclease-capture aptamer Hyg_2
(ATGCCTCCGCTCGAAGTAGTACCGAATCGAAAACGAGTTCAAGGTAC;

SEQ ID NO: 5),
and

Nuclease-capture aptamer Hyg_3
(TCGTCTGGCTAAGATCGGCTACCGAATCGAAAACGAGTTCAAGGTAC;

SEQ ID NO: 6).
```

Figure 4:
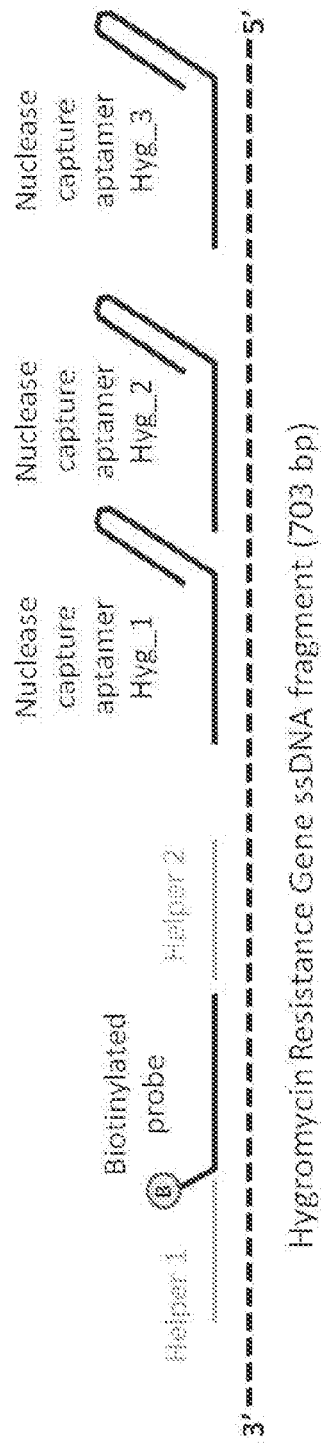
FIG. 4 shows the relative binding positions of each component of a probe—hygromycin resistance gene ssDNA fragment—capture aptamer complex in an embodiment of the method. Helper oligonucleotides were designed to bind adjacent to the biotinylated probe with a separation distance of three nucleotides in order to reduce target secondary structure and aid probe binding.

The biotinylated probe was supplied by Integrated DNA Technologies and the remaining oligonucleotides by Sigma-Aldrich. The relative target-binding position of each of the nucleic acids is shown in FIG. 4.

The nuclease capture assay was performed as follows: a reaction mix comprising 10 µl assymetric PCR reaction product (~450 fmoles hygromycin resistance gene ssDNA fragment); 20 pmoles of each capture structure; 10 pmoles of the biotinylated probe and each helper oligonucleotide; 0.2% SDS (Sigma-Aldrich); 5×SSC buffer (Sigma-Aldrich) and 2×Denhardt's solution (Sigma-Aldrich) was made up to 25 µl with dH$_2$O was incubated at 50° C. for 60 minutes. A control solution containing dH$_2$O instead of the ssDNA target was included. The target and control solutions were subsequently added to solutions of 0.3 mg pre-washed streptavidin-coated M-280 dynabeads (Invitrogen) suspended in 30 µl binding buffer (1M NaCl; 5 mM Tris-HCl pH 7.4; 0.5 mM EDTA; 0.05% Tween-20) and gently agitated for 20 minutes at room temperature. Following the bead-binding reaction, the beads were magnetically retained in the side of the tube and washed three times with 90 µl binding buffer to remove all non-bound reaction components. Subsequently, the beads were resuspended and gently agitated for 5 minutes in an EcoRI reaction solution comprising 4 units EcoRI (New England Biolabs); 1× EcoRI buffer (100 mM Tris-HCl; 50 mM NaCl; 10 mM MgCl$_2$; 0.025% Triton X-100; pH 7.5: New England Biolabs) and 1 mg/ml BSA made up to 50 µl with dH$_2$O. The magnetic beads and any captured EcoRI molecules were removed and 19 µl of the solution was added to two PCR plate wells (Eppendorf) along with 2 µl signaling molecule (Fluorescein-GAGAATTCAGTTTTCTGAATTCTC-Dabcyl; SEQ ID NO: 7; 190 nM final reaction concentration). The reactions were analysed on an Eppendorf Realplex$^2$ Mastercycler Epgradient S real-time PCR machine operating at a constant temperature of 25° C. Fluorescence readings were acquired on the FAM channel at intervals of one minute.

Figure 5:
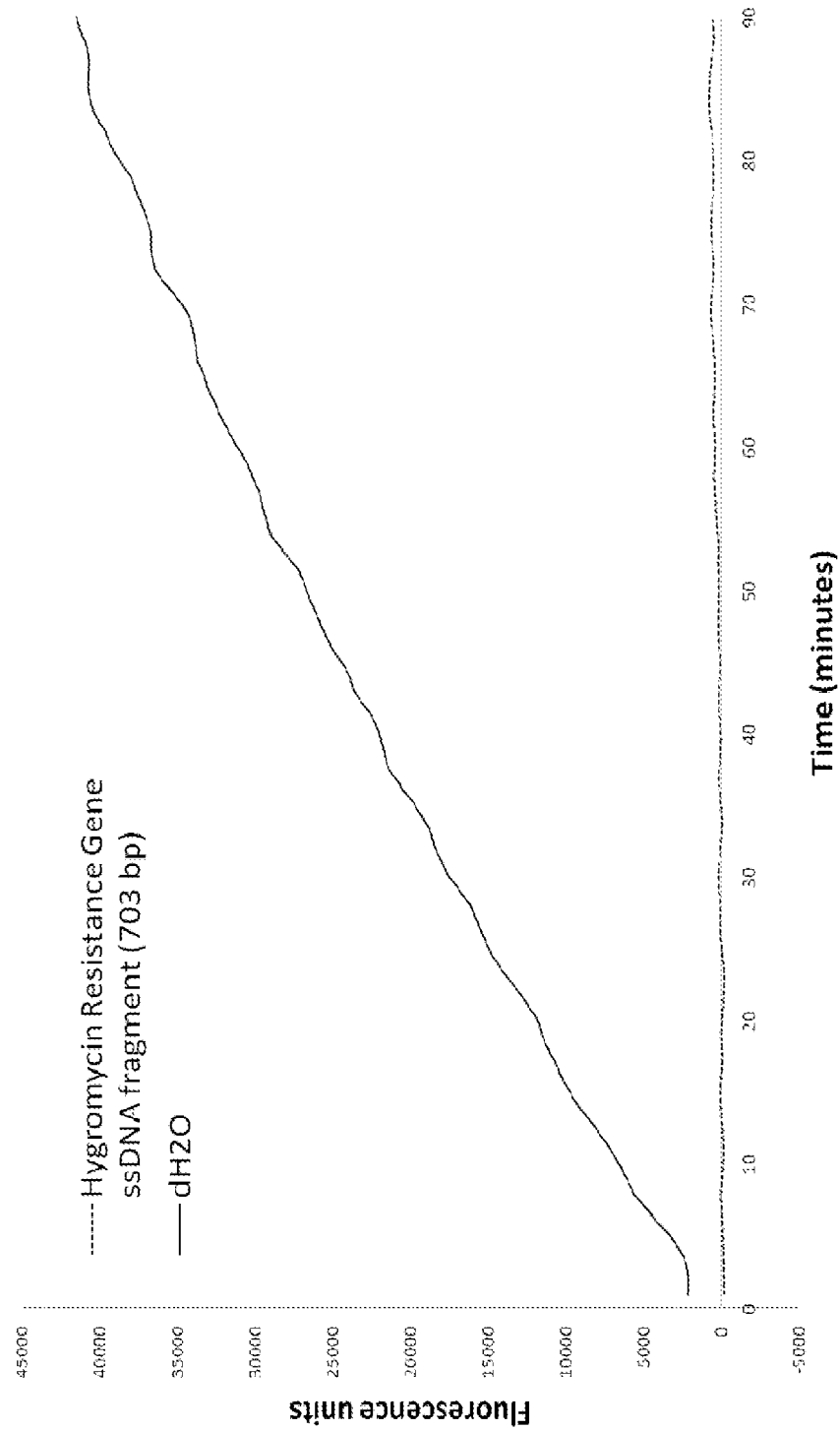
FIG. 5 shows that the presence of the hygromycin resistance gene ssDNA fragment in the sample results in a significant reduction in fluorescence at each acquiring time point relative to the water control. Each smoothed line represents the average of the fluorescence reading of two replicates at each acquiring time point. The presence of the target nucleic acid results in the capture and removal of EcoRI molecules from the reaction solution and thus a reduction in total EcoRI activity as indicated by a reduced rate of signaling molecule digestion relative to the control reaction.
Figure 6:
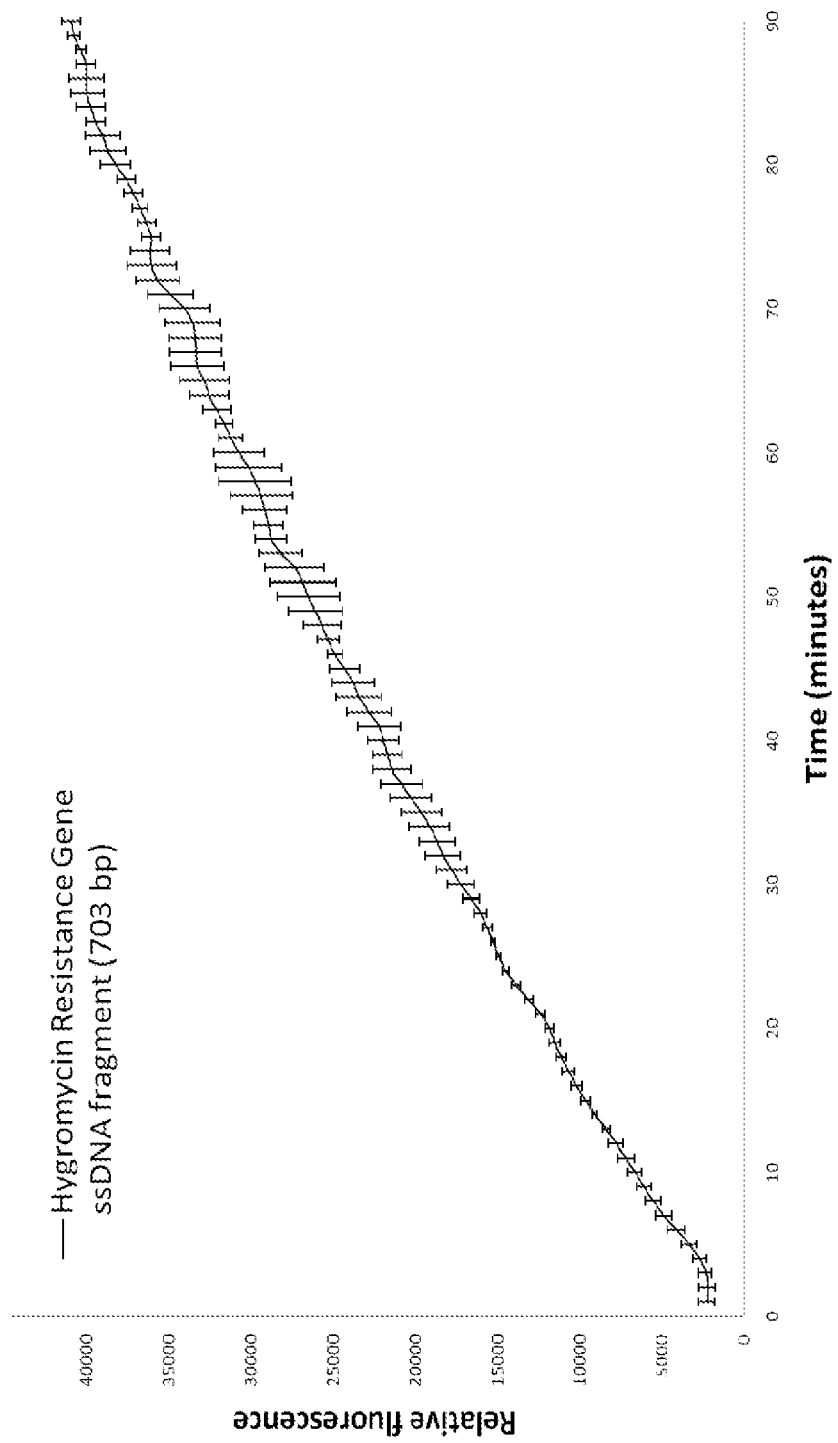
FIG. 6 shows an increase in the control reaction fluorescence relative to the sample reaction florescence at each acquiring time point and indicates the presence of the hygromycin resistance gene ssDNA fragment. The relative fluorescence at each acquiring time point is calculated by subtracting the target treatment fluorescence reading from the water control fluorescence reading. The error bars at each acquiring time point represent ±1 RSD (relative standard deviation).

The averaged data for each treatment are shown in FIG. 5 and the adjusted relative data are shown in FIG. 6. The adjusted relative data was calculated by subtracting the target present fluorescent reading at each acquiring point from the water control reading at each acquiring point. Error bars at each acquiring point represent ±1 RSD (relative standard deviation).

These data indicate that the presence of the single-stranded hygromycin resistance gene ssDNA fragment in the original analyte induces a detectable signal. The very low fluorescence increase over time for the target present treatment demonstrated that the probe—target—capture aptamer complex had formed and captured virtually all EcoRI molecules from solution. The rapid increase in fluorescence over time for the water control reaction indicated that in the absence of the target nucleic acid the nuclease capture aptamers were not retained on the magnetic beads and thus no EcoRI molecules were captured from the reaction mix. Conversion of the raw data to relative fluorescence by subtracting the target present fluorescence reading from the water control reading at each acquiring time point allows for simple visualisation of the increase in relative signal as the reaction proceeds, thus indicating the presence of the target in a standard fashion.

EXAMPLE 3

Detection of RNA

An advantage of the methods of the present invention over techniques such as PCR is that RNA can be directly analysed without the requirement for conversion to cDNA prior to analysis. Specific non-limiting examples are provided in further detail below.

Detection of 18S rRNA

To demonstrate RNA detection, a probe, helper oligonucleotides and capture structures were designed to hybridise to the 18S small ribosomal subunit of *Oryza sativa* (rice). Due to the highly conserved nature of ribosomal RNA (rRNA) sequences among eukaryotes, the probe and capture structure components of the assay were also largely complementary to mammalian 18S rRNA sequences from *Homo sapiens* (human) and *Mus musculus* (mouse).

An assay was conducted with 50 ng total RNA extracted from rice leaf tissue and human and mouse cell lines. The following oligonucleotides were used in the assay:
a biotinylated probe (biotin-TEG-TTTCTCAGGCTC-CCTCTCCGGAATCGAACCCTAATTCT; SEQ ID NO: 8);
five helper oligonucleotides which bind to the target nucleic acid adjacent to the probe and capture structures:

```
Helper 1 (TCACCCGTCACCACCATGGT; SEQ ID NO: 9),

Helper 2 (CCTTCCTTGGATGTGGTAGC; SEQ ID NO: 10),

Helper 3 (GAGGGCCGTGCGATCCGTCG; SEQ ID NO: 11),

Helper 4 (AATGCGCCCCTCCCGGAAGT; SEQ ID NO: 12),

Helper 5 (AATCATCGGATCAGCGGGCG; SEQ ID NO: 13);
``` and
three capture structures comprising nuclease-capture aptamers with target-binding portions:

Nuclease-capture aptamer 18S_1
(AATTTGAATGATGCGTCGCCGGTACCGAATCGAAAACGAGTTCAAGGTA
C; SEQ ID NO: 14), Nuclease-capture aptamer 18S_2
(CCATCGAAAGTTGATAGGGCTACCGAATCGAAAACGAGTTCAAGGTAC;
SEQ ID NO: 15),
and Nuclease-capture aptamer 18S_3
(CCGCGTCAGCCTTTTATCTATACCGAATCGAAAACGAGTTCAAGGTAC;
SEQ ID NO: 16).

Figure 7:
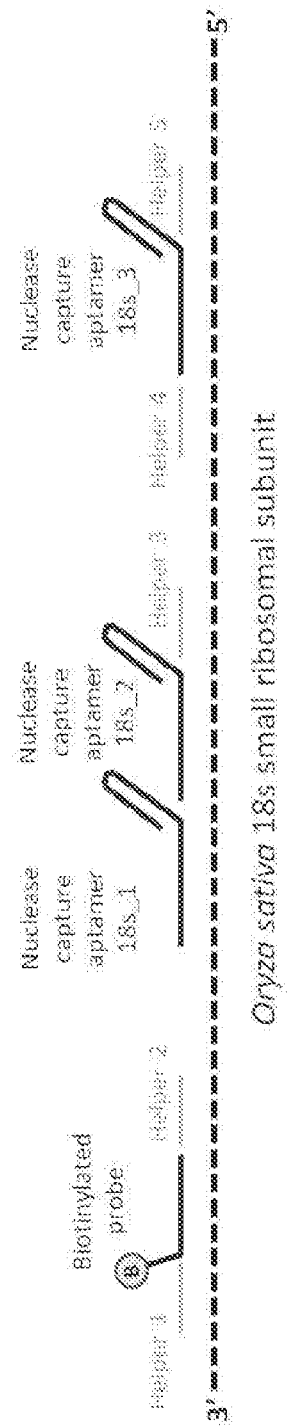
FIG. 7 shows the relative binding positions of each component of the probe—18S rRNA target—capture aptamer complex. Helper oligonucleotides were designed to bind adjacent to the biotinylated probe and nuclease capture aptamers with a separation distance of three nucleotides in order reduce target secondary structure and aid binding.

The biotinylated probe was supplied by Integrated DNA Technologies and the remaining oligonucleotides by Sigma-Aldrich. The relative binding positions of each component are shown in FIG. 7.

Figure 8:
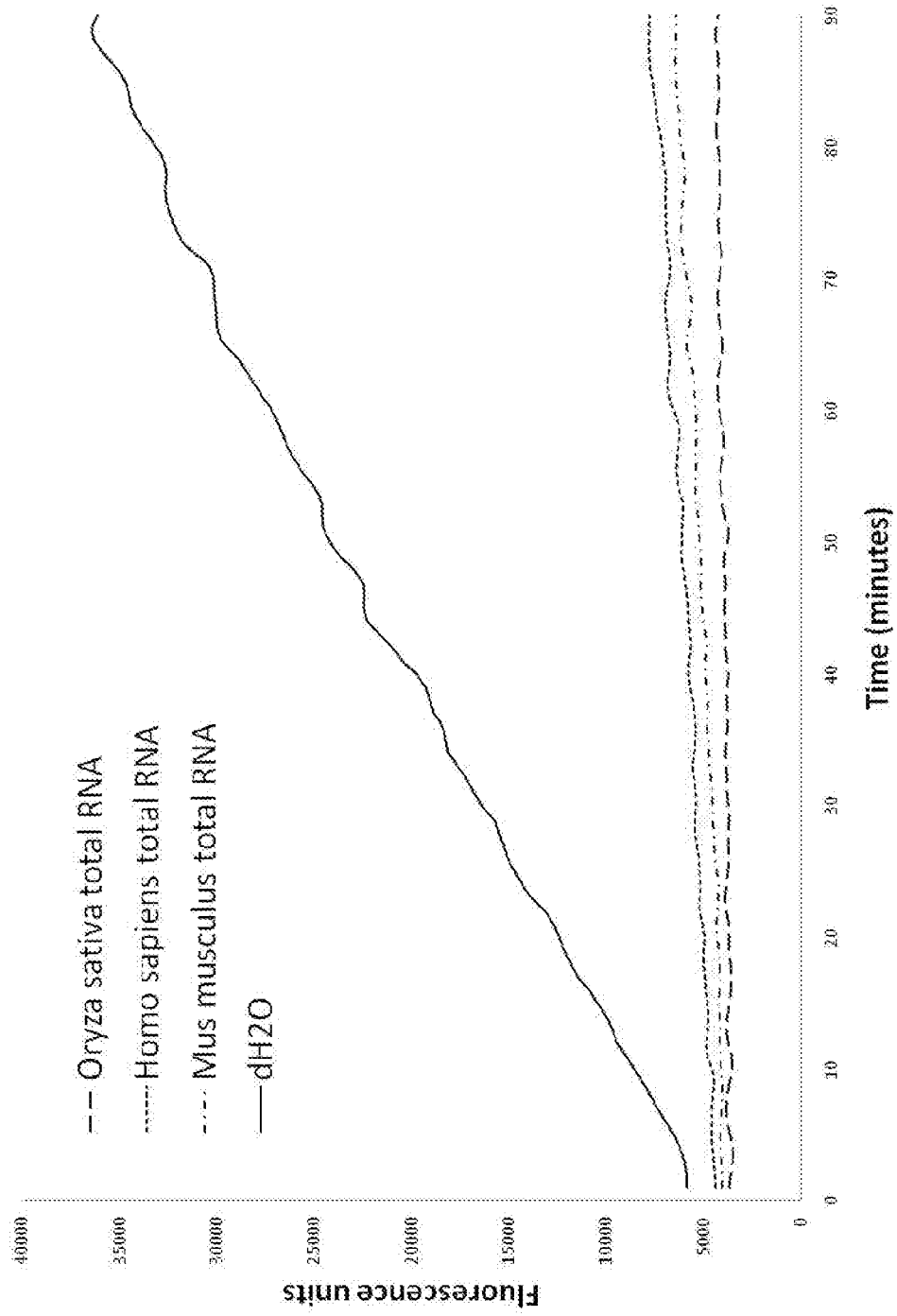
FIG. 8 shows that the presence of 18S rRNA in each total RNA treatment results in a significant reduction in signal relative to the water control treatment. A smooth line for each treatment represents the average of the fluorescence readings of two replicates at each acquiring time point. The presence of the target nucleic acid results in the capture and removal of EcoRI molecules from the reaction solution and thus a reduction in the rate of digestion of fluorescent signaling molecules relative to the water control reaction. The slightly lower signal for rice in comparison to the mammalian samples is likely due to perfect complementarity between the probe, helpers and capture aptamers and the 18S rice rRNA target.
Figure 9:
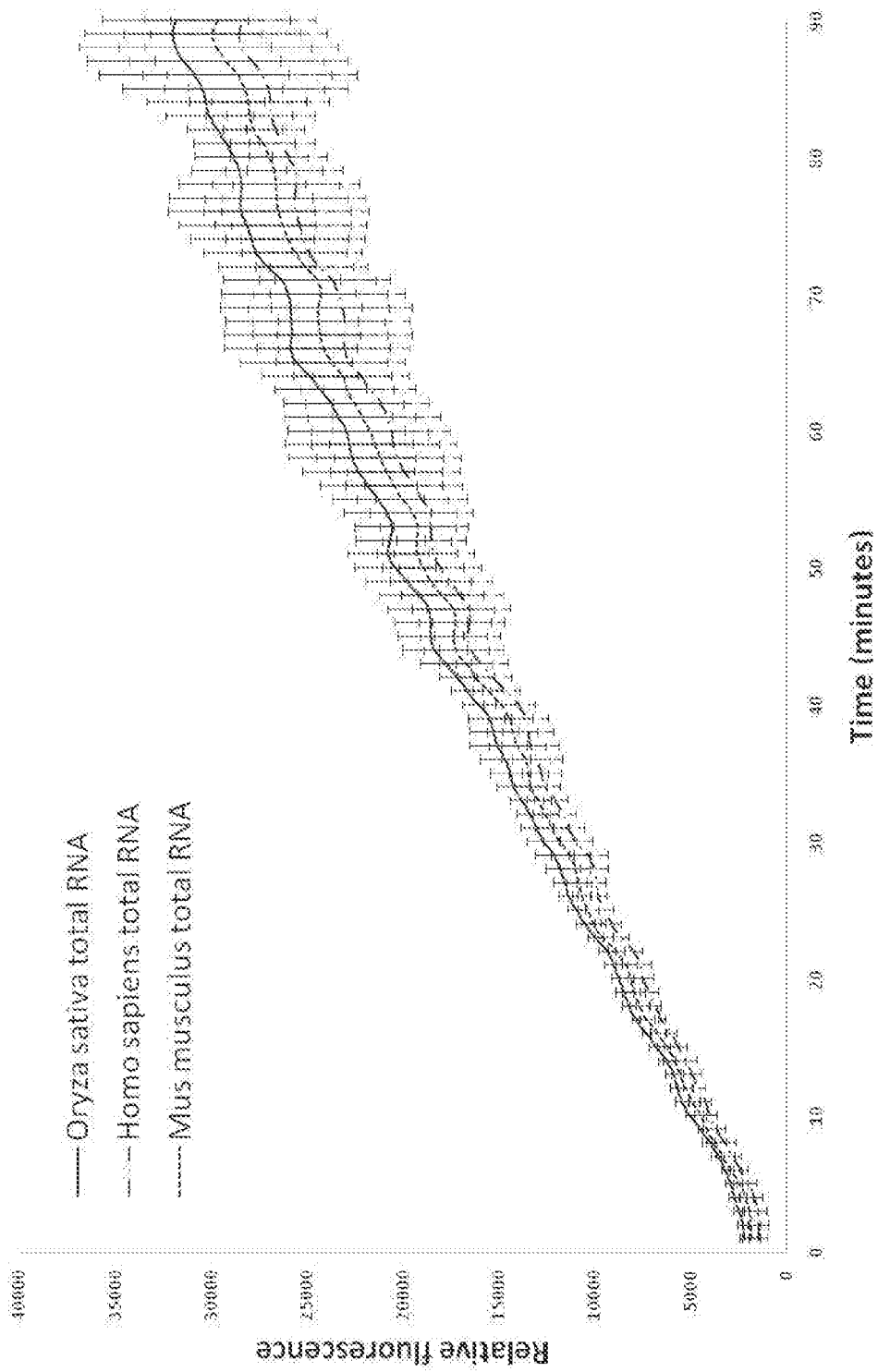
FIG. 9 shows an increase in relative fluorescence over time and indicates the presence of 18S rRNA in each total RNA treatment. Relative fluorescence was calculated by subtracting each total RNA treatment fluorescence reading from the water control reading at each acquiring time point. The error bars at each acquiring time point represent ±1 RSD (relative standard deviation).

The nuclease capture assay was performed with four treatments: rice total RNA; mouse total RNA; human total RNA and a water control. Briefly, a reaction mix was prepared as follows: 50 ng RNA or dH$_2$O was mixed with 20 pmoles of each nuclease capture aptamer; 10 pmoles of the biotinylated probe and each helper oligonucleotide; 0.2% SDS (Sigma-Aldrich); 5×SSC buffer (Sigma-Aldrich); 2×Denhardt's solution (Sigma-Aldrich) and made up to 20 µl with dH$_2$O and incubated at 50° C. for 40 minutes. The remainder of the assay including bead-binding, wash steps and EcoRI capture was performed as previously described. The averaged and relative fluorescent data generated are displayed in FIGS. 8 and 9.

The data indicate that by using the nuclease capture assay, 18S rRNA can be detected in a sample of total RNA extracted from each source. With 50 ng total RNA loaded, virtually all EcoRI molecules have been captured from the reaction mix for the rice RNA treatment and to a slightly lesser extent the human and mouse cell line treatments. The species difference is likely due to reduced complementarity between the probe, helper and capture aptamer binding sites and the 18S rRNA target of the mammalian species. This may result in slightly reducing binding efficiency and thus reduced EcoRI capture.

Figure 10:
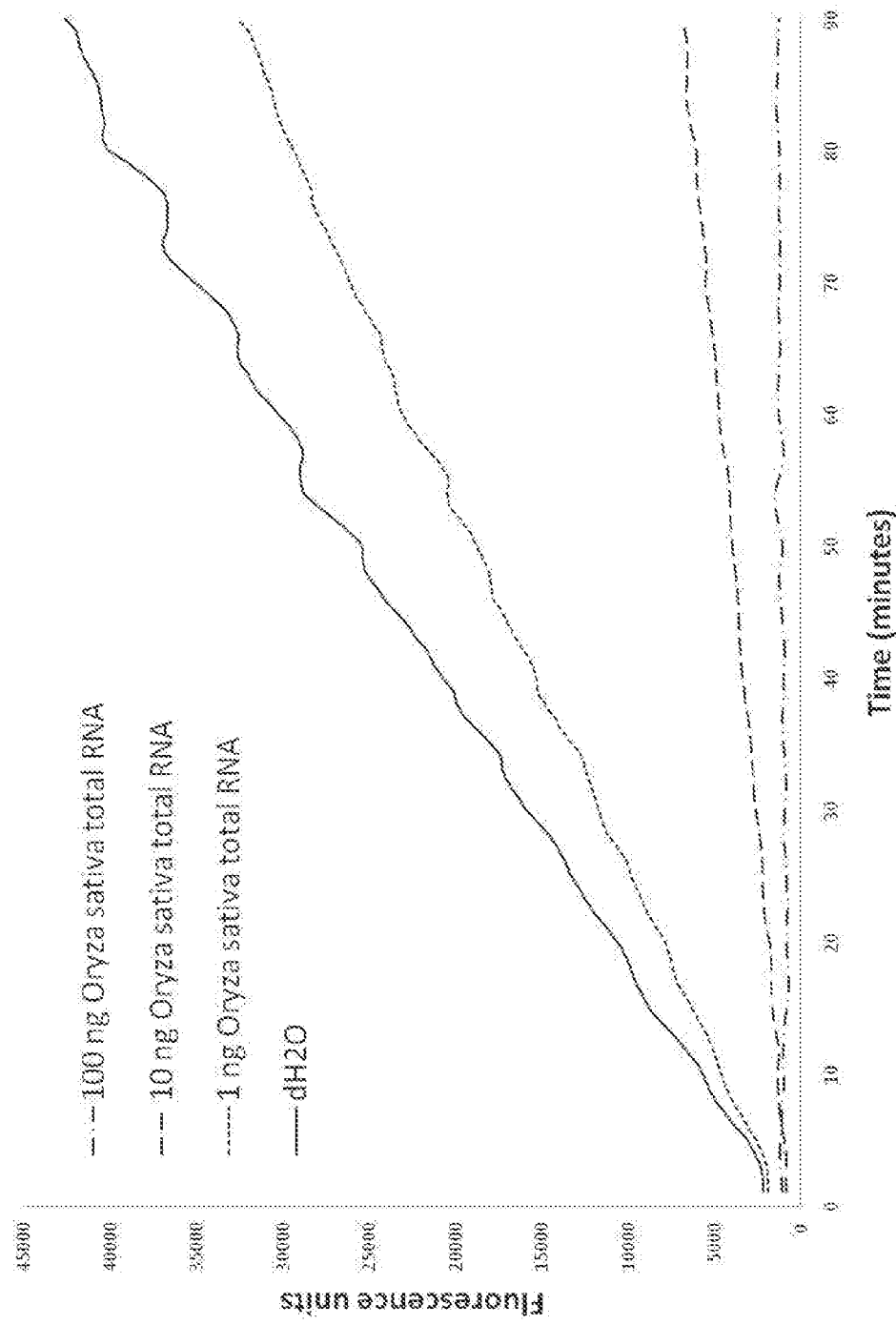
FIG. 10 demonstrates the semi-quantitative nature of the nuclease capture assay for 18S rRNA detection for quantities between 1 ng and 100 ng of total RNA analysed. Each smooth line represents the average of the fluorescence readings of two replicates for each treatment at each acquiring time point.

At specific target nucleic acid concentrations, a portion of rather than all EcoRI molecules are captured and removed from solution. As the amount of EcoRI molecules removed from solution is proportional to the quantity of target nucleic acid molecules present in the original sample, the assay is semi-quantitative over that range of target concentrations. An 18S rRNA detection assay with treatments of 100 ng, 10 ng and 1 ng of total rice RNA was performed as previously described. The data generated demonstrate the semi-quantitative nature of the system (FIGS. 10 and 11).

The data indicate that the detection of 18S rRNA is semi-quantitative between the ranges of 1 ng and 100 ng of total RNA analysed, with the most variation evident between 1 ng and 10 ng. The relative data show a clear increase in the rate of relative signal generation for higher amounts of target rRNA.

Detection of Green Fluorescent Protein (GFP) mRNA

Green fluorescent protein (GFP) is a gene frequently used to mark the presence of genetically modified organisms (GMO). A human cell line that over-expresses GFP was used for this experiment, with GFP expression confirmed using quantitative real-time PCR (data not shown). The affinity biosensor was used to specifically detect GFP mRNA in a sample of total RNA obtained from the human cell line. The assay comprised the following oligonucleotides:

a dual biotinylated probe nucleic acid (dual biotin-GAGAGAGAGATTCATGTGGTCGGGG-TAGCGGCTGAAGCACTGCAC; SEQ ID NO: 17); and 25 nuclease-capture aptamers, 24 of which were specific to the GFP mRNA and one of which bound to the poly-A tail of GFP mRNA:

Nuclease-capture aptamer GFP_1
(CTTGCTCACCATGGTATTAGTACCGAATCGAAAACGAGTTCAAGGTAC;
SEQ ID NO: 18)

Nuclease-capture aptamer GFP_2
(ACACGCTGAACTTGTGGCGTACCGAATCGAAAACGAGTTCAAGGTAC;
SEQ ID NO: 19)

Nuclease-capture aptamer GFP_3
(CCCCTTGTTGAATACGCTTGTACCGAATCGAAAACGAGTTCAAGGTAC;
SEQ ID NO: 20)

Nuclease-capture aptamer GFP_4
(TAGTTGTACTCCAGCTTGTGCCTACCGAATCGAAAACGAGTTCAAGGTA
C; SEQ ID NO: 21)

Nuclease-capture aptamer GFP_5
(TTGAAGAAGATGGTGCGCTCTACCGAATCGAAAACGAGTTCAAGGTAC;
SEQ ID NO: 22)

Nuclease-capture aptamer GFP_6
(AGATCAGATCCCATACAATTACCGAATCGAAAACGAGTTCAAGGTAC;
SEQ ID NO: 23)

Nuclease-capture aptamer GFP_7
(AACTCACAACGTGGCACTGGTACCGAATCGAAAACGAGTTCAAGGTAC;
SEQ ID NO: 24)

Nuclease-capture aptamer GFP_8
(GCAGGTGTATCTTATACACGTACCGAATCGAAAACGAGTTCAAGGTAC;
SEQ ID NO: 25)

Nuclease-capture aptamer GFP_9
(GTAGGTCAGGGTGGTCACGAGGTACCGAATCGAAAACGAGTTCAAGGTA
C; SEQ ID NO: 26)

Nuclease-capture aptamer GFP_10
(CGGACTTGAAGAAGTCGTGCTACCGAATCGAAAACGAGTTCAAGGTAC;
SEQ ID NO: 27)

Nuclease-capture aptamer GFP_11
(GGTACCTTCTGGGCATCCTTTACCGAATCGAAAACGAGTTCAAGGTAC;
SEQ ID NO: 28)

Nuclease-capture aptamer GFP_12
(GGATGTTGCCGTCCTCCTTGTACCGAATCGAAAACGAGTTCAAGGTAC;
SEQ ID NO: 29)

Nuclease-capture aptamer GFP_13
(ATGATATAGACGTTGTGGCTTACCGAATCGAAAACGAGTTCAAGGTAC;
SEQ ID NO: 30)

Nuclease-capture aptamer GFP_14
(GGCACCTGTCGCCAGGTGGGTACCGAATCGAAAACGAGTTCAAGGTAC;
SEQ ID NO: 31)

-continued

Nuclease-capture aptamer GFP_15
(TCAAGAAGCTTCCAGAGGAATACCGAATCGAAAACGAGTTCAAGGTAC;

SEQ ID NO: 32)

Nuclease-capture aptamer GFP_16
(TTGAAGTTCACCTTGTACCGAATCGAAAACGAGTTCAAGGTAC; SEQ

ID NO: 33)

Nuclease-capture aptamer GFP_17
(GTCCTCGATGTTGTGTACCGAATCGAAAACGAGTTCAAGGTAC; SEQ

ID NO: 34)

Nuclease-capture aptamer GFP_18
(TTGGGGTCTTTGCTCATACCGAATCGAAAACGAGTTCAAGGTAC; SEQ

ID NO: 35)

Nuclease-capture aptamer GFP_19
(GTCCATGCCGAGAGTGATTACCGAATCGAAAACGAGTTCAAGGTAC;

SEQ ID NO: 36)

Nuclease-capture aptamer GFP_20
(GCTTTACTTGTACAGTACCGAATCGAAAACGAGTTCAAGGTAC; SEQ

ID NO: 37)

Nuclease-capture aptamer GFP_21
(TAGATGCATGCTCGATACCGAATCGAAAACGAGTTCAAGGTAC; SEQ

ID NO: 38)

Nuclease-capture aptamer GFP_22
(TAGGAATGCTCGTCATACCGAATCGAAAACGAGTTCAAGGTAC; SEQ

ID NO: 39)

Nuclease-capture aptamer GFP_23
(GCTCGAGGTTAACGATACCGAATCGAAAACGAGTTCAAGGTAC; SEQ

ID NO: 40)

Nuclease-capture aptamer GFP_24
(TACCTCAGATCTTCTTACCGAATCGAAAACGAGTTCAAGGTAC; SEQ

ID NO: 41)

Poly-A tail nuclease-capture aptamer GFP_25
(TTTTTTTTTTTTTTTTTTTTTTTTGTACCGAATCGAAAACGAGTTCAA

GGTAC; SEQ ID NO: 42).

Total RNA was obtained from a GFP-positive human cell line using a standard trizol extraction method. Components were added to the target binding reaction at the following final concentrations: 250 nM biotinylated probe; 125 nM each GFP mRNA-specific nuclease-capture aptamer; 1.25 µM poly-A tail nuclease-capture aptamer; 5×SSC buffer (Sigma); 2×Denhardt's buffer (Sigma); 0.2% SDS (Sigma); one to five µg total RNA and water to a total volume of 40 µl. These solutions were incubated at 50° C. for 40 minutes. The solutions were then added to 0.3 mg of pre-washed streptavidin-coated M280 dynabeads (Invitrogen) and agitated for 30 minutes at room temperature. Following the bead-binding reaction, the beads were magnetically retained in the side of the tube and washed three times with 90 µl buffer (1 M NaCl; 5 mM Tris-HCl pH 7.4; 0.5 mM EDTA; 0.05% Tween-20) to remove all non-bound reaction components. Subsequently, the beads were resuspended and gently agitated for 5 minutes in an EcoRI reaction solution comprising 4 units EcoRI (New England Biolabs); 1× EcoRI buffer (100 mM Tris-HCl; 50 mM NaCl; 10 mM $MgCl_2$; 0.025% Triton X-100; pH 7.5: New England Biolabs) and 1 mg/ml BSA made up to 50 µl with d$H_2$O. The magnetic beads and any captured EcoRI molecules were removed and 19 µl of the solution was added to two PCR plate wells (Eppendorf) along with 2 µl signaling molecule (Fluorescein-GAGAATTCAGTTTTCTGAAT-TCTC-Dabcyl; SEQ ID NO: 7; 190 nM final reaction concentration). The reactions were analysed on an Eppendorf Realplex$^2$ Mastercycler Epgradient S real-time PCR machine operating at a constant temperature of 25° C. Fluorescence readings were acquired on the FAM channel at intervals of one minute.

The adjusted relative data for each treatment is shown in FIG. 12, and confirms the specific detection of GFP mRNA between 0.5 µg and 5 µg of total RNA. Therefore, the data indicate that by using the nuclease capture assay, mRNA can be detected (in this example GFP mRNA) in a sample of total RNA (in this example total RNA extracted from a GFP-positive human cell line source). Indeed, after a period of 25 minutes, positive detection of GFP mRNA at each quantity of total RNA is apparent.

Detection of Hygromycin mRNA

The hygromycin resistance gene is a commonly used selection marker employed in the generation of genetically-modified plants. The affinity biosensor allowed for the detection of hygromycin mRNA present in total RNA isolated from hygromycin-positive rice (*Oryza sativa*) leaf tissue. The assay comprised the following oligonucleotides:

a dual-biotinylated probe nucleic acid (dual biotin-CAT-CATCGAAATTGCCGTCAACCAAGCTCTGATAG; SEQ ID NO: 1); and 40 nuclease-capture aptamers, 39 of which were specific to the hygromycin mRNA and one of which bound to the poly-A tail of hygromycin mRNA:

Nuclease-capture aptamer Hyg_1
(AGTCGTGGCGATCCTGCAAGCTCCGTACCGAATCGAAAACGAGTTCAAGG

TAC; SEQ ID NO: 4),

Nuclease-capture aptamer Hyg_2
(ATGCCTCCGCTCGAAGTAGTACCGAATCGAAAACGAGTTCAAGGTAC;

SEQ ID NO: 5),
and

Nuclease-capture aptamer Hyg_3
(TCGTCTGGCTAAGATCGGCTACCGAATCGAAAACGAGTTCAAGGTAC;

SEQ ID NO: 6)

Nuclease-capture aptamer Hyg_4
(GTCTGCTGCTCCATACAAGTACCGAATCGAAAACGAGTTCAAGGTAC;

SEQ ID NO: 43)

Nuclease-capture aptamer Hyg_5
(TGTCCGTCAGGACATTGTTTACCGAATCGAAAACGAGTTCAAGGTAC;

SEQ ID NO: 44)

Nuclease-capture aptamer Hyg_6
(GCATCAGCTCATCGAGAGCTACCGAATCGAAAACGAGTTCAAGGTAC;

SEQ ID NO: 45)

Nuclease-capture aptamer Hyg_7
(GGTGTCGTCCATCACAGTTACCGAATCGAAAACGAGTTCAAGGTAC;

SEQ ID NO: 46)

Nuclease-capture aptamer Hyg_8
(GGATCAGCAATCGCGCATATGTACCGAATCGAAAACGAGTTCAAGGTAC;

SEQ ID NO: 47)

Nuclease-capture aptamer Hyg_9
(AGCGATCGCATCCATAGCCTACCGAATCGAAAACGAGTTCAAGGTAC;
SEQ ID NO: 48)

Nuclease-capture aptamer Hyg_10
(CAGTTCGGTTTCAGGCAGGTTACCGAATCGAAAACGAGTTCAAGGTAC;
SEQ ID NO: 49)

Nuclease-capture aptamer Hyg_11
(CAACGTGACACCCTGTGCATACCGAATCGAAAACGAGTTCAAGGTAC;
SEQ ID NO: 50)

Nuclease-capture aptamer Hyg_12
(CGCTAAACTCCCCAATGTCATACCGAATCGAAAACGAGTTCAAGGTAC;
SEQ ID NO: 51)

Nuclease-capture aptamer Hyg_13
(ACTTCCGGAATCGGGTACCGAATCGAAAACGAGTTCAAGGTAC; SEQ
ID NO: 52)

Nuclease-capture aptamer Hyg_14
(GATGCAAAGTGCCGATATACCGAATCGAAAACGAGTTCAAGGTAC; SEQ
ID NO: 53)

Nuclease-capture aptamer Hyg_15
(ATAACGATCTTTGTAGAATACCGAATCGAAAACGAGTTCAAGGTAC;
SEQ ID NO: 54)

Nuclease-capture aptamer Hyg_16
(ATCGGCGCAGCTATTTATACCGAATCGAAAACGAGTTCAAGGTAC; SEQ
ID NO: 55)

Nuclease-capture aptamer Hyg_17
(CAGGACATATCCACGCCTACCGAATCGAAAACGAGTTCAAGGTAC; SEQ
ID NO: 56)

Nuclease-capture aptamer Hyg_18
(CTACATCGAAGCTGAATACCGAATCGAAAACGAGTTCAAGGTAC; SEQ
ID NO: 57)

Nuclease-capture aptamer Hyg_19
(ACGAGATTCTTCGCCCTCTACCGAATCGAAAACGAGTTCAAGGTAC;
SEQ ID NO: 58)

Nuclease-capture aptamer Hyg_20
(GAGCTGCATCAGGTCGGTACCGAATCGAAAACGAGTTCAAGGTAC; SEQ
ID NO: 59)

Nuclease-capture aptamer Hyg_21
(ACTTCTCGACAGACGTCTACCGAATCGAAAACGAGTTCAAGGTAC; SEQ
ID NO: 60)

Nuclease-capture aptamer Hyg_22
(GTGAGTTCAGGCTTTTACCGAATCGAAAACGAGTTCAAGGTAC; SEQ
ID NO: 61)

Nuclease-capture aptamer Hyg_23
(ACCTCGTATTGGGAATCTACCGAATCGAAAACGAGTTCAAGGTAC; SEQ
ID NO: 62)

Nuclease-capture aptamer Hyg_24
(GAACATCGCCTCGCTCCATACCGAATCGAAAACGAGTTCAAGGTAC;
SEQ ID NO: 63)

Nuclease-capture aptamer Hyg_25
(CTCCGGATCGGACGATTTACCGAATCGAAAACGAGTTCAAGGTAC; SEQ
ID NO: 64)

Nuclease-capture aptamer Hyg_26
(TTTGTGTACGCCCGACAGTTACCGAATCGAAAACGAGTTCAAGGTAC;
SEQ ID NO: 65)

Nuclease-capture aptamer Hyg_27
(CAGACGGCCGCGCTTCTTACCGAATCGAAAACGAGTTCAAGGTAC; SEQ
ID NO: 66)

Nuclease-capture aptamer Hyg_28
(ACTTCTACACAGCCATCGTACCGAATCGAAAACGAGTTCAAGGTAC;
SEQ ID NO: 67)

Nuclease-capture aptamer Hyg_29
(GTTTCCACTATCGGCGTACCGAATCGAAAACGAGTTCAAGGTAC;
SEQ ID NO: 68)

Nuclease-capture aptamer Hyg_30
(TGGTCAAGACCAATGCGGAGCTACCGAATCGAAAACGAGTTCAAGGTAC;
SEQ ID NO: 69)

Nuclease-capture aptamer Hyg_31
(TCGCATCGACCCTGCGCCCAAGTACCGAATCGAAAACGAGTTCAAGGTA
C; SEQ ID NO: 70)

Nuclease-capture aptamer Hyg_32
(GTCTGCTGCTCCATACAAGTACCGAATCGAAAACGAGTTCAAGGTAC;
SEQ ID NO: 71)

Nuclease-capture aptamer Hyg_33
(ATGACCGCTGTTATGCGGTACCGAATCGAAAACGAGTTCAAGGTAC;
SEQ ID NO: 72)

Nuclease-capture aptamer Hyg_34
(GAAATCCGCGTGCACGATACCGAATCGAAAACGAGTTCAAGGTAC; SEQ
ID NO: 73)

Nuclease-capture aptamer Hyg_35
(TTCGGGGCAGTCCTCGGCCCTACCGAATCGAAAACGAGTTCAAGGTAC;
SEQ ID NO: 74)

Nuclease-capture aptamer Hyg_36
(CCAGTGATACACATACCGAATCGAAAACGAGTTCAAGGTAC; SEQ ID
NO: 75)

Nuclease-capture aptamer Hyg_37
(GATTCCTTGCGGTCCGAATGTACCGAATCGAAAACGAGTTCAAGGTAC;
SEQ ID NO: 76)

Nuclease-capture aptamer Hyg_38
(AGCGATCGCATCCATAGCCTACCGAATCGAAAACGAGTTCAAGGTAC;
SEQ ID NO: 77)

Nuclease-capture aptamer Hyg_39
(GCGACCGGTTGTAGAACAGCTACCGAATCGAAAACGAGTTCAAGGTAC;
SEQ ID NO: 78)

Poly-A tail nuclease-capture aptamer Hyg_40
(TTTTTTTTTTTTTTTTTTTTTTTTTTGTACCGAATCGAAAACGAGTTCAA
GGTAC; SEQ ID NO: 79)

Total RNA was obtained from a hygromycin-positive rice leaf tissue using a standard trizol extraction method. Components were added to the target binding reaction at the following final concentrations: 250 nM biotinylated probe; 125 nM each hygromycin mRNA-specific nuclease-capture aptamer; 1.25 µM poly-A tail nuclease-capture aptamer; 5×SSC buffer (Sigma); 2×Denhardt's buffer (Sigma); 0.2% SDS (Sigma); one or two µg total RNA and water to a total volume of 40 µl. These solutions were incubated at 50° C. for 40 minutes. The solutions were then added to 0.3 mg of pre-washed streptavidin-coated M280 dynabeads (Invitrogen) and agitated for 30 minutes at room temperature. Following the bead-binding reaction, the beads were magnetically retained in the side of the tube and washed three times with 90 ul buffer (1 M NaCl; 5 mM Tris-HCl pH 7.4; 0.5 mM EDTA; 0.05% Tween-20) to remove all non-bound reaction components. Subsequently, the beads were resuspended and gently agitated for 5 minutes in an EcoRI reaction solution comprising 4 units EcoRI (New England Biolabs); 1× EcoRI buffer (100 mM Tris-HCl; 50 mM NaCl; 10 mM $MgCl_2$; 0.025% Triton X-100; pH 7.5: New England Biolabs) and 1 mg/ml BSA made up to 50 µl with $dH_2O$. The magnetic beads and any captured EcoRI molecules were removed and 19 µl of the solution was added to two PCR plate wells (Eppendorf) along with 2 µl signaling molecule (Fluorescein-GAGAATTCAGTTTTCTGAAT-TCTC-Dabcyl; SEQ ID NO: 7; 190 nM final reaction concentration). The reactions were analysed on an Eppendorf $Realplex^2$ Mastercycler Epgradient S real-time PCR machine operating at a constant temperature of 25° C. Fluorescence readings were acquired on the FAM channel at intervals of one minute.

The adjusted relative data for each treatment is shown in FIG. 13, and confirms the specific detection of hygromycin mRNA in 1 µg and 2 µg of total RNA. The specificity of the affinity biosensor can be evidenced by the negative control of hygromycin-negative bacterial total RNA where virtually no signal is apparent. Therefore, the data indicate that by using the nuclease capture assay, mRNA can be detected (in this example hygromycin mRNA) in a sample of total RNA (in this example total RNA extracted from rice leaf tissue). Indeed, after a period of 10 minutes, positive detection of hygromycin mRNA at each quantity of total RNA is apparent.

EXAMPLE 4

Conjugation of Probe to a Solid Substrate

In addition to hybridising the assay components in solution prior to their addition to a solution of streptavidin-coated magnetic beads, the probe oligonucleotide can be covalently conjugated to magnetic beads and the conjugate added directly to the binding reaction. This reduces the quantity of experimental steps along with total assay time as the bead-complex binding step is no longer required. To demonstrate the effectiveness of probe-conjugated beads, a comparative assay with streptavidin-coated beads and biotinylated probe was performed.

Prior to conducting the assay, an amine-tagged version of the 18S probe (amine-12C-TTTCTCAGGCTCCCTCTC-CGGAATCGAACCCTAATTCT; SEQ ID NO: 80) was conjugated to M-270 carboxylic acid Dynabeads (Invitrogen) with an EDC crosslinker (Thermo Scientific) using the manufacturer's protocol. Non-conjugated probe oligonucleotides were removed via two binding buffer wash steps prior to the addition of the conjugate-beads to the sandwich binding reaction. For comparison, the assay was performed using the biotin-TEG 18S probe and streptavidin-coated M280 magnetic beads as previously described. Treatments for each assay included the presence of 5 ng total RNA and a water control. Five ng of total RNA was chosen for the assay quantity as the amount of 18S target present is in the semi-quantitative dynamic range of the biosensor. For the probe-bead conjugate treatments, capture aptamers, helpers and buffer constituents were added to 30 µl of washed conjugated beads at the same quantities and concentrations as described previously. Complex formation took place at 50° C. in an Eppendorf Thermomixer shaking at 1100 rpm for 60 minutes. Bead washing, EcoRI capture and analysis were performed as previously described for all treatments.

The data for each treatment indicate that the use of covalent probe-bead conjugates has no detrimental effect on assay sensitivity, with the target present and water control treatment for each bead-binding type virtually identical (see FIGS. 14 and 15).

EXAMPLE 5

Use of 18S rRNA as Scaffold

An additional method of capturing multiple nuclease molecules for each target nucleic acid is via the capture of a separate nucleic acid molecule that could be synthetic or endogenous to the sample being tested such as 18S ribosomal RNA (rRNA) molecules.

18S rRNA is highly abundant in total eukaryotic RNA extractions, making up approximately 20% of the RNA extracted. Detection of 18S rRNA has previously been demonstrated using the nuclease capture assay. In the earlier examples, multiple nuclease-capture aptamers were hybridised to each 18S rRNA molecule.

For a nucleic acid target other than 18S rRNA, an oligonucleotide linker or series of oligonucleotide linkers with an 18S rRNA binding portion and a target binding portion can be added to the reaction mix, along with multiple nuclease-capture aptamers that bind to 18S rRNA. The presence of the target nucleic acid allows for the co-purification of one or more 18S rRNA molecules with multiple hybridised nuclease-capture aptamers (see FIG. 16). These embodiments utilise abundant and conserved endogenous cellular RNA molecules to amplify the signal generated by the presence of the target nucleic acid.

In the above embodiments, the 18S rRNA generally serves the function of a scaffold to which multiple capture agents may bind.

In these embodiments, the process of the re-designing individual nuclease-capture aptamers with target binding moieties is avoided, along with the addition of support structures for the nuclease capture aptamers. Rather, in these embodiments, target specificity is conferred by a targeting portion which binds to both the target nucleic acid and the 18S rRNA scaffold.

To provide proof-of-concept for the oligonucleotide scaffold approach, a biosensor assay was performed with single-stranded DNA containing the hygromycin sequence used as a target (as used in Example 2). The assay consisted of the following oligonucleotides:

a dual-biotinylated probe nucleic acid (dual biotin-CAT-CATCGAAATTGCCGTCAACCAAGCTCTGATAG; SEQ ID NO: 1);

two helper oligonucleotides:

```
Helper 1 (TGGTCAAGACCAATGCGGAGC; SEQ ID NO: 2);
and

Helper 2 (TCGCATCGACCCTGCGCCCAAG; SEQ ID NO: 3);
``` five linkers, each with a hygromycin target-binding moiety and an 18S rRNA-binding moiety:

```
Hygromycin 18S rRNA linker 1
(TTTCTCAGGCTCCCTCTCCGGAATCGAACCCTAATTCTTGCAAGTCGTGG

CGATCCTGCAAGCTCCG; SEQ ID NO: 81)

Hygromycin 18S rRNA linker 2
(CTCTCCGGAATCGAACCCTAATTCTTGCAAGTCGTGGCGATCCTGCAAGC

TCCG; SEQ ID NO: 82)

Hygromycin 18S rRNA linker 3
(TTTCTCAGGCTCCCTCTCCGGAATCGAACCCTAATTCTTTCATGTTAGTC

GTGGCGATCCTGCAAGCTCCG; SEQ ID NO: 83)

Hygromycin 18S rRNA linker 4
(TTTCTCAGGCTCCCTCTCCGGAATCGAACCCTAATTCTAGTCGGTGTCGT

CCATCACAGTTTGCCAGTGATA; SEQ ID NO: 84)

Hygromycin 18S rRNA linker 5
(TTTCTCAGGCTCCCTCTCCGGAATCGAACCCTAATTCTTTGAAGCGATCG CATCCATAGCCTCCGCGACCGG; SEQ ID NO: 85);
and
``` ten 18S-specific nuclease-capture aptamers:

```
Nuclease-capture aptamer 18S_4
(AATTTGAATGATGCGTCGCCGGTACCGAATCGAAAACGAGTTCAAGGTA

C; SEQ ID NO: 86)

Nuclease-capture aptamer 18S_5
(CCATCGAAAGTTGATAGGGCTACCGAATCGAAAACGAGTTCAAGGTAC;

SEQ ID NO: 87)

Nuclease-capture aptamer 18S_6
(CCGCGTCAGCCTTTTATCTATACCGAATCGAAAACGAGTTCAAGGTAC;

SEQ ID NO: 88)

Nuclease-capture aptamer 18S_7
(GATTTAATGAGCCATTCGCAGTTTTACCGAATCGAAAACGAGTTCAAGGT

AC; SEQ ID NO: 89)

Nuclease-capture aptamer 18S_8
(GTTATTTATTGTCACTACCTACCGAATCGAAAACGAGTTCAAGGTAC;

SEQ ID NO: 90

Nuclease-capture aptamer 18S_9
(GCACCAGACTTGCCCTCCAATACCGAATCGAAAACGAGTTCAAGGTAC;

SEQ ID NO: 91)

Nuclease-capture aptamer 18S_10
(TGCAACAACTTAAATATACGTACCGAATCGAAAACGAGTTCAAGGTAC;

SEQ ID NO: 92)
```

```
-continued
Nuclease-capture aptamer 18S_11
(GTGCCTGCCGTGAGGCGGACTACCGAATCGAAAACGAGTTCAAGGTAC;

SEQ ID NO: 93)

Nuclease-capture aptamer 18S_12
(CGATGGCTTGCTTTGAGCACTACCGAATCGAAAACGAGTTCAAGGTAC;

SEQ ID NO: 94)

Nuclease-capture aptamer 18S_13
(TCACCCGTCACCACCATGGTTACCGAATCGAAAACGAGTTCAAGGTAC;

SEQ ID NO: 95).
```

The hygromycin single-stranded (ss) DNA target was generated as previously described in Example 2. Components were added to the target binding reaction at the following final concentrations: 500 nM biotinylated probe; 500 nM Helper 1 and Helper 2; 50 nM each hygromycin-18S linker; 500 nM each 18S-binding nuclease-capture aptamer; 5×SSC buffer (Sigma); 2×Denhardt's buffer (Sigma); 0.2% SDS (Sigma); 0 (negative control) or 1 µl single-stranded DNA target and water to a total volume of 40 µl. These solutions were incubated at 50° C. for 40 minutes. The solutions were then added to 0.3 mg of pre-washed streptavidin-coated M280 dyna-beads (Invitrogen) and agitated for 30 minutes at room temperature. Following the bead-binding reaction, the beads were magnetically retained in the side of the tube and washed three times with 90 ul buffer (1M NaCl; 5 mM Tris-HCl pH 7.4; 0.5 mM EDTA; 0.05% Tween-20) to remove all non-bound reaction components. Subsequently, the beads were resuspended and gently agitated for 5 minutes in an EcoRI reaction solution comprising 4 units EcoRI (New England Biolabs); 1× EcoRI buffer (100 mM Tris-HCl; 50 mM NaCl; 10 mM $MgCl_2$; 0.025% Triton X-100; pH 7.5: New England Biolabs) and 1 mg/ml BSA made up to 50 µl with $dH_2O$. The magnetic beads and any captured EcoRI molecules were removed and 19 µl of the solution was added to two PCR plate wells (Eppendorf) along with 2 µl signaling molecule (Fluorescein-GAGAATTCAGTTTTCTGAATTCTC-Dabcyl; SEQ ID NO: 7; 190 nM final reaction concentration). The reactions were analysed on an Eppendorf Realplex$^2$ Mastercycler Epgradient S real-time PCR machine operating at a constant temperature of 25° C. Fluorescence readings were acquired on the FAM channel at intervals of one minute.

The adjusted relative data for the hygromycin ssDNA target is shown in FIG. 17. The data indicates that by using the oligonucleotide scaffold approach, hygromycin ssDNA can be positively detected after a period of as little as 10 minutes.

EXAMPLE 6

Capturing Multiple Nuclease Molecules

Nano-Sphere Approach

As indicated above with respect to FIG. 3C, an embodiment of the invention involves the capture of multiple nuclease molecules for each copy of the target nucleic acid using a scaffold such as a nano-sphere. In order to demonstrate this, nano-spheres were used to co-purify multiple capture aptamers for each target-binding event. For proof-of-concept, 18S rRNA was again selected as a target and M-270 Dynabeads (Invitrogen) covalently conjugated to the 18S probe were used. This allowed for the use of streptavidin-coated 40 nm latex nanospheres (Invitrogen), which could be bound to multiple capture aptamers through the biotin-streptavidin interaction.

The assay was successfully performed using a sequential process. Initially, the Dynabead-probe conjugate, the RNA analyte and biotinylated capture probe were hybridised and unbound components removed with a wash step. Subsequently, the streptavidin-coated nano-spheres were added for binding to the remaining target-bound capture probes, with unbound nano-spheres then removed in a wash step. Finally, biotinylated capture aptamers were added for binding to the remaining captured nano-spheres, with unbound capture aptamers also removed via a wash step. The reminder of the assay was performed as described previously.

To demonstrate the effectiveness of the nano-sphere approach on real-world samples, an assay was carried out with 100 ng rice total RNA (containing the target 18S rRNA) and 100 ng *E. coli* (18S-negative) RNA as a control. The presence of 18S rRNA in the analyte was successfully determined as shown in FIG. 18.

Amine-labeled 18S probes (amine-12C-TTTCTCAG-GCTCCCTCTCCGGAATCGAACCCTAATTCT; SEQ ID NO: 80) were covalently conjugated to carboxylic acid-coated M-270 Dynabeads using an EDC cross-linker following the manufacturer's protocol (See Example 4). Components were added to the target binding reaction at the following final concentrations: 10 µl resuspended dynabead-18S probe conjugate; 1 µM biotinylated capture probe (CGAAAGTTGATAGGGCAGAAATTTGAAT-GATGCGT-Biotin-TEG; SEQ ID NO: 96); 5×SSC buffer (Sigma); 2×Denhardt's buffer (Sigma); 0.2% SDS (Sigma); 100 ng target or control total RNA and water to a total volume of 30 µl. These solutions were agitated at room temperature for 30 minutes. Following the binding reaction, the beads were magnetically retained in the side of the tube and washed three times with 90 µl buffer (1M NaCl; 5 mM Tris-HCl pH 7.4; 0.5 mM EDTA; 0.05% Tween-20) to remove all non-bound reaction components. The beads were resuspended in 30 µl of the same buffer supplemented with 1 µl Fluo-Spheres® NeutrAvidin® labeled nonfluorescent 40 nm nano-spheres followed by agitation at room temperature for 20 minutes. Following two washes with the same buffer, the biotinylated 18S capture aptamer (Biotin-TCTG-GAATTTGAAGCCCTGGGATACCGAATC-GAAAACGAGTTCAAGGTA; SEQ ID NO: 97) was added to a final concentration of 1 µM in 30 µl buffer. Again, two washes with the same buffer to remove unbound components were performed. Subsequently, the beads were resuspended and gently agitated for 5 minutes in an EcoRI reaction solution comprising 4 units EcoRI (New England Biolabs); 1× EcoRI buffer (100 mM Tris-HCl; 50 mM NaCl; 10 mM $MgCl_2$; 0.025% Triton X-100; pH 7.5: New England Biolabs) and 1 mg/ml BSA made up to 50 µl with $dH_2O$. The magnetic beads and any captured EcoRI molecules were removed and 19 µl of the solution was added to two PCR plate wells (Eppendorf) along with 2 µl signaling molecule (Fluorescein-GAGAATTCAGTTTTCTGAATTCTC-Dabcyl; SEQ ID NO: 7; 190 nM final reaction concentration). The reactions were analysed on an Eppendorf Realplex$^2$ Mastercycler Epgradient S real-time PCR machine operating at a constant temperature of 25° C. Fluorescence readings were acquired on the FAM channel at intervals of one minute.

The adjusted relative data for the 18S rRNA target is shown in FIG. 18. The data indicates that by using the nano-sphere approach 18S rRNA can be detected in 100 ng of total RNA extracted from rice leaf tissue. Indeed, after a period of 25 minutes positive detection of 18S rRNA was apparent.

Those skilled in the art will appreciate that the invention described herein is susceptible to variations and modifications other than those specifically described. It is to be understood that the invention includes all such variations and modifications. The invention also includes all of the steps, features, compositions and compounds referred to, or indicated in this specification, individually or collectively, and any and all combinations of any two or more of the steps or features.

The invention claimed is:

1. A method for detecting a target nucleic acid in a sample, the method comprising forming a reaction mix comprising:
   the sample;
   a nuclease;
   a solid substrate;
   a probe nucleic acid which is hybridisable under the conditions of the method to a first portion of the target nucleic acid, wherein the probe nucleic acid is immobilisable on the solid substrate; and
   a capture structure comprising a capture portion which is able to capture the nuclease and a targeting portion comprising a nucleotide sequence which is hybridisable under the conditions of the method to a second portion of the target nucleic acid;
   wherein the presence of the target nucleic acid in the sample allows the formation of a complex on the solid substrate wherein the complex comprises the probe nucleic acid, the target nucleic acid, the capture structure and a captured nuclease; and
   determining the extent of complex formation comprising measuring a residual nuclease activity in the reaction mix, wherein the extent of the residual nuclease activity is negatively correlated with the extent of complex formation, and wherein the extent of complex formation is positively correlated with the presence of the target nucleic acid in the sample.

2. The method of claim 1, wherein the target nucleic acid comprises DNA or RNA.

3. The method of claim 2, wherein the target nucleic acid comprises RNA.

4. The method of claim 3, wherein the target nucleic acid comprises rRNA or mRNA.

5. The method of claim 1, wherein the target nucleic acid is in a single-stranded state when contacted with the probe nucleic acid and the capture structure.

6. The method of claim 1, wherein the nuclease is a restriction endonuclease.

7. The method of claim 1, wherein the nuclease is EcoRI.

8. The method of claim 1, wherein the capture portion of the capture structure comprises an aptamer.

9. The method of claim 1, wherein the method further comprises the addition of one or more helper oligonucleotides which bind to the target nucleic acid at a site adjacent to the binding site of the probe nucleic acid and/or a capture structure.

10. The method of claim 9, wherein the binding site of the helper oligonucleotide on the target nucleic acid is separated from the binding site of the probe nucleic acid and/or a capture structure by a distance of three nucleotide residues.

11. The method of claim 1, wherein determining the extent of complex formation further comprises measuring a nuclease activity associated with the complex, wherein the extent of nuclease activity associated with the complex is positively correlated with the extent of complex formation.

12. The method of claim 11, wherein the method further comprises displacement of the nuclease from the complex and measurement of the displaced nuclease activity.

13. The method of claim 1, wherein a nuclease activity is determined by the rate or extent of cleavage of a reporter nucleotide sequence.

14. The method of claim 1, wherein the complex comprises a plurality of capture portions.

15. The method of claim 1, wherein multiple capture structures can bind to the target nucleic acid.

16. The method of claim 15, wherein the multiple capture structures can bind to the target nucleic acid at multiple positions on the target nucleic acid.

17. The method of claim 1, wherein the capture structure further comprises a scaffold to which a plurality of capture portions can bind.

18. The method of claim 17, wherein the scaffold comprises a nucleic acid or a solid substrate.

* * * * *